(12) United States Patent
Lowe et al.

(10) Patent No.: US 9,797,000 B2
(45) Date of Patent: Oct. 24, 2017

(54) NON-TARGET AMPLIFICATION METHOD FOR DETECTION OF RNA SPLICE-FORMS IN A SAMPLE

(75) Inventors: Brian Lowe, Olney, MD (US); Anna K. Fulbright, Columbia, MD (US); Irina Nazarenko, Gaithersburg, MD (US)

(73) Assignee: QIAGEN GAITHERSBURG INC., Gaithersburg, MD (US)

( * ) Notice: Subject to any disclaimer, the term of this patent is extended or adjusted under 35 U.S.C. 154(b) by 140 days.

(21) Appl. No.: 12/771,042

(22) Filed: Apr. 30, 2010

(65) Prior Publication Data
US 2010/0311039 A1    Dec. 9, 2010

Related U.S. Application Data

(60) Provisional application No. 61/174,938, filed on May 1, 2009, provisional application No. 61/174,946, filed on May 1, 2009.

(51) Int. Cl.
*C12Q 1/68* (2006.01)

(52) U.S. Cl.
CPC ........... *C12Q 1/6804* (2013.01); *C12Q 1/682* (2013.01)

(58) Field of Classification Search
None
See application file for complete search history.

(56) References Cited

U.S. PATENT DOCUMENTS

| | | |
|---|---|---|
| 4,486,536 A | 12/1984 | Baker et al. |
| 4,486,539 A | 12/1984 | Ranki et al. |
| 4,563,417 A | 1/1986 | Albarella et al. |
| 4,563,419 A | 1/1986 | Ranki et al. |
| 4,689,294 A | 8/1987 | Boguslawski et al. |
| 4,731,325 A | 3/1988 | Palva et al. |
| 4,732,847 A | 3/1988 | Stuart et al. |
| 4,743,535 A | 5/1988 | Carrico |
| 4,751,177 A | 6/1988 | Stabinsky et al. |
| 4,775,619 A | 10/1988 | Urdea |
| 4,833,084 A | 5/1989 | Carrico |
| 4,851,330 A | 7/1989 | Kohne et al. |
| 4,865,980 A | 9/1989 | Stuart et al. |
| 4,868,105 A | 9/1989 | Urdea et al. |

(Continued)

FOREIGN PATENT DOCUMENTS

| | | |
|---|---|---|
| CN | 101351564 A | 1/2009 |
| EP | 0 163 220 | 12/1985 |

(Continued)

OTHER PUBLICATIONS

Yan et al. (1996) The J. of Biol Chem. vol. 271 No. 41: pp. 25699-25706.*

(Continued)

*Primary Examiner* — Samuel Woolwine
(74) *Attorney, Agent, or Firm* — McBee Moore Woodward & Vanik IP, LLC; Susan McBee

(57) ABSTRACT

Provided are methods of isolating RNA from a biological sample, methods and means for determining the presence of particular RNA splice-form variants in a biological sample, methods and means for determining the relative ratio of RNA ratios in a biological sample, and methods and means for predicting the progression of precancerous cervical lesions.

9 Claims, 7 Drawing Sheets

(56) References Cited

U.S. PATENT DOCUMENTS

| | | |
|---|---|---|
| 4,889,798 A | 12/1989 | Rabbani |
| 4,894,325 A | 1/1990 | Englehardt et al. |
| 5,082,830 A | 1/1992 | Brakel et al. |
| 5,106,727 A | 4/1992 | Hartley et al. |
| 5,116,734 A | 5/1992 | Higgs et al. |
| 5,200,313 A | 4/1993 | Carrico |
| 5,288,611 A | 2/1994 | Kohne et al. |
| 5,374,524 A | 12/1994 | Miller et al. |
| 5,424,413 A | 6/1995 | Hogan et al. |
| 5,437,977 A | 8/1995 | Segev |
| 5,474,895 A | 12/1995 | Ishii et al. |
| 5,484,699 A | 1/1996 | Bouma et al. |
| 5,545,806 A | 8/1996 | Lonberg et al. |
| 5,545,807 A | 8/1996 | Surani et al. |
| 5,556,748 A | 9/1996 | Douglas |
| 5,614,362 A | 3/1997 | Urdea et al. |
| 5,623,049 A | 4/1997 | Lobberding et al. |
| 5,627,030 A | 5/1997 | Pandian et al. |
| 5,629,153 A | 5/1997 | Urdea |
| 5,629,156 A | 5/1997 | Shah et al. |
| 5,635,352 A | 6/1997 | Urdea et al. |
| 5,641,630 A | 6/1997 | Snitman |
| 5,656,731 A | 8/1997 | Urdea |
| 5,681,697 A | 10/1997 | Urdea et al. |
| 5,681,897 A | 10/1997 | Silvis et al. |
| 5,695,926 A | 12/1997 | Cros et al. |
| 5,702,893 A | 12/1997 | Urdea et al. |
| 5,728,531 A | 3/1998 | Yamada et al. |
| 5,731,153 A | 3/1998 | Lucas et al. |
| 5,736,316 A | 4/1998 | Irvine et al. |
| 5,747,244 A | 5/1998 | Sheridan et al. |
| 5,747,248 A | 5/1998 | Collins |
| 5,750,338 A | 5/1998 | Collins et al. |
| 5,759,773 A | 6/1998 | Tyagi et al. |
| 5,786,183 A | 7/1998 | Ryder et al. |
| 5,792,606 A | 8/1998 | Deger et al. |
| 5,800,994 A | 9/1998 | Martinelli et al. |
| 5,814,492 A | 9/1998 | Carrino et al. |
| 5,821,339 A | 10/1998 | Schafer et al. |
| 5,827,661 A | 10/1998 | Blais |
| 5,853,993 A | 12/1998 | Dellinger et al. |
| 5,888,724 A | 3/1999 | Silverstein et al. |
| 5,981,179 A | 11/1999 | Lorinez et al. |
| 5,994,079 A | 11/1999 | De La Rosa et al. |
| 6,010,895 A | 1/2000 | Deacon et al. |
| 6,027,897 A | 2/2000 | Lorincz et al. |
| 6,043,038 A | 3/2000 | Sivaraja et al. |
| 6,057,099 A | 5/2000 | Nathan et al. |
| 6,083,925 A | 7/2000 | Li et al. |
| 6,110,676 A | 8/2000 | Coull et al. |
| 6,110,682 A | 8/2000 | Dellinger et al. |
| 6,110,687 A | 8/2000 | Nilsen |
| 6,207,385 B1 | 3/2001 | Stanley |
| 6,221,581 B1 | 4/2001 | Engelhardt et al. |
| 6,225,053 B1 | 5/2001 | Garcia et al. |
| 6,228,578 B1 | 5/2001 | Impraim et al. |
| 6,228,580 B1 | 5/2001 | Blumenfeld et al. |
| 6,232,462 B1 | 5/2001 | Collins et al. |
| 6,268,128 B1 | 7/2001 | Collins et al. |
| 6,277,579 B1 | 8/2001 | Lazar et al. |
| 6,280,954 B1 | 8/2001 | Ulfendahl |
| 6,326,136 B1 | 12/2001 | Lazar et al. |
| 6,355,424 B1 | 3/2002 | Lorincz et al. |
| 6,436,662 B1 | 8/2002 | Mielzynska et al. |
| 6,521,190 B1 | 2/2003 | Edens et al. |
| 6,544,732 B1 | 4/2003 | Chee et al. |
| 6,583,278 B1 | 6/2003 | Carter |
| 6,686,151 B1 | 2/2004 | Lazar et al. |
| 6,828,098 B2 | 12/2004 | Langmore et al. |
| 6,890,729 B2 | 5/2005 | Mielzynska et al. |
| 6,969,585 B2 | 11/2005 | Lorincz et al. |
| 6,977,148 B2 | 12/2005 | Dean et al. |
| 7,001,776 B2 | 2/2006 | Botacini Das Dores et al. |
| 7,371,518 B2 | 5/2008 | Lorincz et al. |
| 7,439,016 B1 * | 10/2008 | Anthony .............. C12Q 1/6834 435/6.1 |
| 7,601,497 B2 | 10/2009 | Nazarenko et al. |
| 7,812,144 B2 | 10/2010 | Karlsen |
| 8,012,944 B2 | 9/2011 | Lacasse et al. |
| 2001/0055766 A1 | 12/2001 | Aristarkhov et al. |
| 2002/0012936 A1 | 1/2002 | Lorincz et al. |
| 2003/0096232 A1 | 5/2003 | Kris et al. |
| 2003/0108897 A1 | 6/2003 | Drmanac |
| 2003/0175765 A1 | 9/2003 | Kessler et al. |
| 2003/0175789 A1 | 9/2003 | Weininger et al. |
| 2004/0180362 A1 | 9/2004 | Lazar et al. |
| 2004/0214302 A1 | 10/2004 | Anthony et al. |
| 2005/0026976 A1 | 2/2005 | Curtin et al. |
| 2005/0032038 A1 | 2/2005 | Fisher et al. |
| 2005/0032105 A1 | 2/2005 | Bair et al. |
| 2005/0119217 A1 | 6/2005 | Lacasse et al. |
| 2005/0147996 A1 | 7/2005 | Sorge |
| 2006/0051809 A1 * | 3/2006 | Nazarenko et al. .............. 435/6 |
| 2006/0160188 A1 | 7/2006 | Kurnit et al. |
| 2006/0240449 A1 | 10/2006 | McGlennen et al. |
| 2007/0109898 A1 | 5/2007 | Kasai |
| 2007/0154884 A1 | 7/2007 | Lorincz |
| 2007/0292899 A1 | 12/2007 | Lovell et al. |
| 2008/0200344 A1 | 8/2008 | Cheng |
| 2008/0247914 A1 | 10/2008 | Edens et al. |
| 2009/0032445 A1 | 2/2009 | Doak et al. |
| 2009/0263819 A1 | 10/2009 | Muraca |
| 2009/0286687 A1 | 11/2009 | Dressman et al. |
| 2009/0298187 A1 | 12/2009 | Nazarenko et al. |
| 2010/0081124 A1 | 4/2010 | Abravaya et al. |
| 2010/0311039 A1 | 12/2010 | Lowe et al. |
| 2011/0009277 A1 | 1/2011 | Devos et al. |
| 2014/0087449 A1 | 3/2014 | Ballhause et al. |

FOREIGN PATENT DOCUMENTS

| | | | |
|---|---|---|---|
| EP | 0 167 366 B1 | 1/1986 | |
| EP | 0 281 927 B1 | 9/1988 | |
| EP | 0 288 737 A1 | 11/1988 | |
| EP | 0333465 | 9/1989 | |
| EP | 0 336 454 B1 | 11/1992 | |
| EP | 0 144 914 A2 | 6/1995 | |
| EP | 0 415 978 B1 | 3/1996 | |
| EP | 0 703 296 A1 | 3/1996 | |
| EP | 118676 A2 * | 7/2001 | .............. C12Q 1/24 |
| EP | 1 806 410 A2 | 7/2007 | |
| EP | 2 184 368 A1 | 5/2010 | |
| JP | T H-07-505759 A | 6/1995 | |
| JP | 200400508019 A | 3/2004 | |
| JP | T-2007-509861 A | 4/2007 | |
| JP | 2009 106220 | 5/2009 | |
| WO | 8607387 | 12/1986 | |
| WO | 88/03957 | 6/1988 | |
| WO | 91/08312 A1 | 6/1991 | |
| WO | 93/10263 A1 | 5/1993 | |
| WO | 84/02721 | 7/1994 | |
| WO | 95/17430 A1 | 6/1995 | |
| WO | 96/40992 | 5/1996 | |
| WO | 97/05277 | 2/1997 | |
| WO | 97/10364 | 3/1997 | |
| WO | 97/31256 A2 | 8/1997 | |
| WO | 98/18488 | 5/1998 | |
| WO | 98/22620 | 5/1998 | |
| WO | 98/59044 A1 | 12/1998 | |
| WO | 99/02488 | 1/1999 | |
| WO | 99/32654 A1 | 7/1999 | |
| WO | 99/36571 A2 | 7/1999 | |
| WO | 99/49224 | 9/1999 | |
| WO | 99/50459 A2 | 10/1999 | |
| WO | 00/60116 A1 | 10/2000 | |
| WO | 01/36681 | 5/2001 | |
| WO | 01/96608 A1 | 12/2001 | |
| WO | 0196608 | 12/2001 | |
| WO | 02/10449 | 2/2002 | |
| WO | 02066993 A1 | 8/2002 | |
| WO | 2004/087950 | 10/2004 | |
| WO | 2005042030 A1 | 5/2005 | |
| WO | 2005/080602 A2 | 9/2005 | |

(56) References Cited

FOREIGN PATENT DOCUMENTS

| | | |
|---|---|---|
| WO | 2005/088311 A1 | 9/2005 |
| WO | 2006039563 A2 | 4/2006 |
| WO | 2006/124771 | 11/2006 |
| WO | 2006/124771 A2 | 11/2006 |
| WO | 2007/056723 | 5/2007 |
| WO | 2007/056723 A3 | 5/2007 |
| WO | 2007/130519 A2 | 11/2007 |
| WO | 2007/134252 A1 | 11/2007 |
| WO | 2008/036061 | 3/2008 |
| WO | 2008/139938 A1 | 11/2008 |
| WO | 2008149237 A2 | 12/2008 |
| WO | 2009/015159 | 1/2009 |
| WO | 2009/057993 A1 | 5/2009 |
| WO | 2009/123996 | 10/2009 |
| WO | 2010/004251 A1 | 1/2010 |
| WO | 2010/028382 | 3/2010 |
| WO | 2010/127228 | 11/2010 |
| WO | 2010/127228 A1 | 11/2010 |

OTHER PUBLICATIONS

Vaeteewoottacharn et al. (Jun. 16, 2005) Virology Journal 2:50 available on line doi:10.1186/1743-422x-2-50).*
Lund et al. (1988) Nucl. Acids Res. vol. 16 (22) 10861-10880. doi:10.1093/nar/16.22.10861. (abstract provided).*
Safarik et al. (1999) J of Chromatography B. vol. 722 p. 33-53.*
Bergemann et al. (1999) Journal of magnetism and magnetic materials 194: 45-52.*
Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.
Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.
Malloy C, et al., "HPV DNA Testing: Technical and Programmatic Issues for Cervical Cancer Prevention in Low-Resource Settings," Path, Dec. 2000.
Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031. Nov. 1995.
Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).
Bohm S, et al., "The Predominant mRNA Class in HPV16-Infected Genital Neoplasias does not Encode the E6 or the E7 Protein," Int. J. Cancer: 55, 791-798 (1993).
Middleton, K, et al., "Organization of Human Papillomavirus Productive Cycle during Neoplastic Progression Provides a Basis for Selection of Diagnostic markers," Journal of Virology, Oct. 2003, pp. 10186-10201.
Stoler, M, et al., "Human Papillomavirus Type 16 and 18 Gene Expression in Cervical Neoplasias," Human Pathol. 23 (1992), pp. 117-128.
Higgins, G, et al., "Transcription patterns of human papillomavirus type 16 in genital intraepithelial neoplasia: evidence for promoter usage within the E7 open reading frame during epithelial differentiation," J. Gen. Virol. 73(1992), pp. 2047-2057.
Karlsen, F, et al., "Use of Multiple PCR Primer Sets for Optimal Detection of Human Papillomavirus," J. Clin. Microbiol. 34 (1996), pp. 2095-2100.
Park, JS, et al., "Physical Status and Expression of HPV Genes in Cervical Cancers," Gynec. Oncol. 95 (1997), pp. 121-129.
Broker, TR, et al., "A Molecular Portrait of Human Papillomavirus Carcinogenesis," Cancer Cells 7 (1989), pp. 197-207.
Letter dated Jan. 6, 2010 to EPO re EP 1 038 022 (46 pages).
Letter to EPO dated Mar. 2, 209 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Partial International Search Report for PCT/US2009/062061, mail date Jan. 5, 2010.
Partial International Search Report for PCT/US2009/062041, mail date Jan. 5, 2010.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) and Poly(I) Poly(dC) As Immunogens for the Induction of Antibodies to RNA-DNA Hybrids," Molecular Immunology, vol. 19, No. 3, pp. 413-420, 1982.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.
Jakobovits et al., "Germ-line transmission and expression of a human-derived yeast artificial chromosome," pp. 255-258, Nature, vol. 362, Mar. 18, 1993.
International Search Report for PCT/US2009/041033, dated Dec. 22, 2009.
Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1), pp. 17-27—see table 3.
GenBank Accession No. K02718, "Human papillomavirus type 16 (HPV16), complete genome.", Mar. 18, 1994. See http://www.ncbi.nlm.nihgov/nuccore/333031.
GenBank Accession No. X74479, "human papillomavirus type 45 genomic DNA.", Apr. 18, 2005. See http://www.ncbi.nlm.nih.gov/nuccore/397022.
GenBank Accession No. X05015, "Human papillomavirus type 18 E6, E7, El, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002. See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999, See http://www.ncbi.nlm.nih.gov/nuccore/333087.
GenBank Accession No. X74481, "Human papillomavirus type 52 genomic DNA.", Apr. 18, 2005. See http://www.ncbi.nlm.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.

(56) References Cited

OTHER PUBLICATIONS

GenBank Accession No. X77858, "Human papillomavirus type 59, complete viral genome.", Apr. 18, 2005. See http://www.ncbi.nlm.nih.gov/nuccore/557236.
GenBank Accession No. U31794, "Human papillomavirus type 66, complete genome.", Oct. 18, 1995. See http://www.ncbi.nlm.nih.gov/nuccore/1020290.
GenBank Accession No. X67161, "Human papillomavirus type L1 gene for major capsid protein.", Apr. 18, 2005. See http://www.ncbi.nlm.nih.gov/nuccore/1197494.
GenBank Accession No. AB027021, "Human papillomavirus type 82 DNA, complete genome.", Jun. 22, 2000. See http://www.ncbi.nlm.nih.gov/nuccore/6970427.
Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517, see the whole document.
Lowe, et al., "A computer program for selection of oligonucleotide primers for polymerase chain reactions", Nucleic Acid Res., vol. 18, No. 7, pp. 1757-1761 (1990).
International Search Report for PCT/US2009/062041, Patent Cooperation Treaty, Mar. 31, 2010 (17 pages).
International Search Report and Written Opinion of PCT/US2010/022264 dated Jun. 7, 2010 (19 pages).
Cohenford et al., "C-195. Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "Chlamydia DNA Test Kit," (Jun. 6, 2008), XP002578832, Retrieved from the Internet: URL: http://www.gentechin.com/chlamydiatestkit.htm.
Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.
Darwin et al., "Comparison of Digene Hybrid Capture 2 and Conventional Culture for Detection of Chlamydia trachomatis and Neisseria gonorrhoeae in Cervical Specimens," Journal of Clinical Microbiology, (Feb. 2002), pp. 641-644, vol. 40, No. 2, XP002578833.
Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6. (Note that the page number of this literature listed on the ISR is incorrect).
Vernick et al., "The HPV DNA virus hybrid capture assay: What is it- and where do we go from here?" MLO Med. Lab. Obs., (Mar. 2003), pp. 8-10, 13, vol. 35, No. 3.
Supplementary European Search Report of PCT/US2006/060603, dated Jul. 7, 2010 (8 pages).
International Search Report and Written Opinion of PCT/US2010/048714, dated Dec. 10, 2010 (14 pages).
International Preliminary Report on Patentability and Written Opinion of PCT/US2009/041033, dated Oct. 19, 2010 (pages).
International Search Report and Written Opinion of PCT/US2010/047769, dated Nov. 9, 2010 (11 pages).
Pachowics, et al., "Sequence specific large volume sample prep solution utilizing Hybrid Capture technology," 41st Annual Oak Ridge Conference; Baltimore, MD; Apr. 16, 2009; retrieved from the Internet: http://www.aacc.org/events/meeting_proceeding/2009/Documents/OakRidge09AllPosters.pdf.
Keegan et al., "Comparison of HPV detection technologies: Hybrid capture 2, PreTect HPV—Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nazarenko et al., "A novel method of HPV genotyping using Hybrid Capture sample preparation method combined with GP5+/6+ PCR and multiplex detection on Luminex XMAP," Journal of Virological Methods, Dec. 1, 2008, pp. 76-81, vol. 154, No. 1-2, Elsevier BV, XP025680302.
Taha et al., "Universal Collection Medium (UCM) is as suitable as the Standard Transport Medium (STM) for Hybrid Capture II (HC-2) assay," Journal of Virological Methods, May 1, 2006, pp. 32-35, vol. 36, No. 1, Elsevier BV, XP025178639.
Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott-Raven Publishers, XP008011933.
Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.
Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.
Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.
Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.
Coquillard et al., "Quantification of intracellular HPV E6/E7 mRNA expression increases the specificity and positive predictive value of cervical cancer screening compared to HPV DNA," Gynecologic Oncology, Jan. 2011, vol. 120, Issue 1, pp. 89-93, Elsevier, Inc.
Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.
Partial European Search Report of EP10185824; mailed Feb. 16, 2011 (8 pages).
Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.
Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.
International Search Report and Written Opinion of PCT/US2011/22887, dated Jun. 1, 2011.
International Preliminary Report on Patentability and Written Opinion of PCT/US2009/062061, dated May 12, 2011.

(56) References Cited

OTHER PUBLICATIONS

International Preliminary Report on Patentability and Written Opinion of PCT/US2009/062041, dated May 12, 2011.
GenBank Submission FJ429103. 2009 [Retrieved from the Internet May 20, 2011: <URL:http://www.ncbl.nlm.nih.gov/nuccore/FJ429103.1>]; in entirety.
Zientara et al., 1998 "Use of reverse transcriptase-polymerase chain reaction (RT-PCR) and dot-blot hybridization for the detection and identification of African horse sickness virus nucleic acids" Arch Virol 14:317-327.
Mansy et al., 1999 "A PCR Based DNA Hybridisation Capture System for the Detection of Human Cytomegalovirus. A Comparative Study with Other Identification Methods" Journal of Virological Methods 80:113-122.
Poulsen et al., 1999 "Detection of Clinical Vancomycin-Resistant Enterococci in Denmark by Multiplex PCR and Sandwich Hybridization" APMIS 107:404-12.
Sjoroos et al., 1998 "Time-Resolved Fluorometry Based Sandwich Hybridisation Assay for HLA-DQA1 Typing" Disease Markers 14:9-19.
Edman et al., 2000 "Pathogen Analysis and Genetic Predisposition Testing Using Microelectronic Arrays and Isothermal Amplification" Journal of Investigative Medicine, 48:93-101.
Monteiro et al.,1997 Evaluation of Performances of Three DNA Enzyme Immunoassays for Detection of Helicobacter pylon PCR Products from Biopsy Specimens Journal of Clinical Microbiology, 35:2931-2936.
Chiu et al., 1998 "Sandwich-type Deoxyribonucleic Acid Hybridization Assays Based on Enzyme Amplified Time-Resolved Fluorometry" Analyst , 123:1315-1319.
White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.
Zammatteo et al., 1997 "Comparison between Microwell and Bead Supports for the Detection of Human Cytomegalovirus Amplicons by Sandwich Hybridization" Analytical Biochemistry 253:180-189.
Fisher et al., 1997 "A System for the Quantitation of DNA Using a Microtiter Plate-Based Hybridization and Enzyme Amplification Technology" Analytical Biochemistry 251:280-287.
Wicks et al., 1998 "A Sandwich Hybridization Assay Employing Enzyme Amplification for Determination of Specific Ribosomal RNA from Unpurified Cell Lysates" Analytical Biochemistry 259:258-264.
Bruckner-Lea et al., 2000 "Rotating Rod Renewable Microcolumns for Automated, Solid-Phase DNA Hybridization Studies" Anal. Chem. 72:4135-4141.
Allen et al., 1998 "High Resolution Genetic Typing of the Class II HLA-DRB 1 Locus Using Group-Specific Amplification and SSO-Hybridisation in Microplates" Hereditas 129:161-167.
Chomvarin et al., 2000 "Development of EIA for Detection of Chlamydia Trachomatis in Genital Specimens" The Southeast Asian Journal of Tropical Medicine and Public Health, 31:96-103.
Alexandre et al., 1998 "Quantitative Determination of CMV DNA Using a Combination of Competitive PCR Amplification and Sandwich Hybridization" BioTechniques, 25: 676-683.
Casademont et al., 2000 "Rapid Detection of Campylobacter fetus by Polymerase Chain Reaction Combined With Non-Radioactive Hybridization Using an Oligonucleotide Covalently Bound to Microwells" Molecular and Cellular Probes 14:233-240.
Hara et al., "Small Sample Whole-Genome Amplification," Optics East 2005, UCRL-PROC-216415, Lawrence Livermore National Laboratory, Oct. 21, 2005.
Brigotti, et al., Nucleic Acids Res., vol. 26, No. 18, pp. 4306-4307, 1998.
PCT/US2009/062061, International Searching Authority, Oct. 26, 2009 (6 pages).
PCT/US2009/062041, International Searching Authority, Oct. 26, 2009 (5 pages).
U.S. Appl. No. 12/588,304, titled "Automated Assay and System," filed Oct. 9, 2009 (not yet published).
U.S. Appl. No. 12/588,306, titled "Open Platform Automated Sample Processing System," filed Oct. 9, 2009 (not yet published).
U.S. Appl. No. 12/622,131, titled "Multiple-Input Analytical System," filed Nov. 19, 2009 (not yet published).
U.S. Appl. No. 12/605,540, titled "Fast Results Hybrid Capture Assay and System," filed Oct. 26, 2009 (not yet published).
U.S. Appl. No. 12/605,605, titled "Fast Results Hybrid Capture Assay on an Automated Platform," filed Oct. 26, 2009 (not yet published).
Bhan et al."2', 5'-Linked oligo-3'-deoxyribonucleoside phosphorothioate chimeras: thermal stability and antisense inhibition of gene expression," Nucleic Acids Research, 1997, vol. 25, No. 16, pp. 3310-3317 (XP-002560367).
Genetech Diagnostics Pvt. Ltd., "Digene HBV Test Hybrid Capture II," Jun. 6, 2008 (XP-002560368).
Hantz et al., "Evaluation of accuracy of three assays for human papillomavirus detection and typing: Hybrid Capture 2, HPV Consensus kit and Amplicor HPV," Pathologie Biologie, Feb. 2008, vol. 56, No. 1, pp. 29-35 (XP002560369).
Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146 (XP002560370).
Boston Bioproducts Inc., "Protein Extraction buffers," Sep. 2, 2007 (XP002560371).
Bart "General Principles of Immunoprecipitation," Jul. 31, 2008 (XP002560372).
Broker et al., "A Molecular Portrait of Human Papillomavirus Carcinogenesis", Cancer Cells, vol. 7, pp. 197-208, 1989 (Roche EU Opposition).
Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).
Karlsen et al., "Use of Multiple PCR Primer Sets for Optimal Detection of Human Papillomavirus", Journal of Clinical Microbiology, pp. 2095-2100, Sep. 1996 (Roche EU Opposition).
Park et al., "Physical Status and Expression of HPV Genes in Cervical Cancers", Gynecologic Oncology, vol. 65, pp. 121-129, 1997 (Roche EU Opposition).
Stoler et al., "Human Papillomavirus Type 16 and 18 Gene Expression in Cervical Neoplasias", Human Pathology, vol. 23, No. 2, pp. 117-128, Feb. 1992 (Roche Eu Opposition).
De Villiers et al., "Classification of Papillomaviruses", Virology, vol. 324, pp. 17-27, 2004.
Howley et al., "A Rapid Method for Detecting and Mapping Homology between Heterologous DNAs", Journal of Biological Chemisny, vol. 254, No. 11, pp. 4879-4883, Jun. 10, 1979.
Law et al., "Conserved Polynucleotide Sequences Among the Genomics of Papillomaviruses", Journal of Virology, vol. 32, No. 1, pp. 199-207, Oct. 1979.
Heilman et al., "Cloning of Human Papilloma Virus Genomic DNAs and Analysis of Homologous Polynucleotide Sequences", Journal of Virology, vol. 36, No. 2, pp. 395-407, Nov. 1980.
Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.
Lorincz, A.T., "Molecular Methods for the Detection of Human Papillomavirus Infection", Obstetrics and Gynecology Clinics of North America, vol. 23, No. 3, pp. 707-730, Sep. 1996.
B.D. Hames, et al., "Nucleic Acid Hybridization. A Practical Approach." 1985.
Greg T. Hermanson, et al., "Immobilized Affinity Ligand Techniques." 1992.
Richard F. Taylor, "Protein Immobilization. Fundamentals and Applications." 1991.

(56) References Cited

OTHER PUBLICATIONS

Blair et al. "Herpes Simplex Virus Viron Stimulatory Protein mRNA Leader Contains Sequence Elements Which Increase Both Virus-Induced Transcription and tnRNA Stability," Journal of Virology, vol. 61, No. 8, pp. 2499-2508, Aug. 1987.
Brendan et al. "Related Functional Domains in Virus DNA Polymerases," The EMBO Journal. vol. 6, No. 1, pp. 160-175, 1987.
Chandler et al., Detection of Dengue-2 Viral RNA by Reversible Target Capture Flybridization., J. Clin. Microbiol., vol. 31 (10), pp. 2641-2647, 1993.
Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Microbiol., vol. 37, No. 4, pp. 958-963, 1999.
Murakami et al., Fluorescent-Labeled Oligonucleotide Probes: Detection of Hybrid Formation in Solution by Fluorscence Polarization Spectroscopy, Nucleic Acids Res., vol. 19 (15), pp. 4097-4102, 1991.
Dunn and Hassell: "A Novel Method to Map Transcripts: Evidence for Homology between an Adenovirus niRNA and Discrete Multiple Regions of the Viral Genome" Cell, 12:23-36, Sep. 1977.
Coutlee et al., "Nonisotopic Detection of RNA in an Enzyme Imunoassay using a Monoclonal Antibody Against DNA-RNA Hybrids" Analytical Biochemistry 181:153-162, 1989.
Chen et al., "DNA Optical Sensor: A Rapid Method for the Detection of DNA Hybridization" Biosensors & Bioelectronics 13:451-458, 1998.
Chevrier et al., "Isolation of a Specific DNA fragment and Development of a PCR Based Method for the Detection of *Mycobacterium genavense*" FEMS Immunology and Medical Microbiology 23:243-452, 1999.
Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 26:5581-5588, 1998.
Gelmetti et al., "Detection of Rabbit Haemorrhagic Disease Virus (RHDV) by In Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detection of *Salmonella* by Using the Colorimetric DNA/rRNA Sandwich Hybridization in Microtiter Wells". J. Vet. Med. Sci. 62:615-619, 2000.
Lazar et al., 1999 "Hybrid Capture®: a Sensitive Signal Amplification-based Chemiluminescent Test for the Detection and Quantitation of Human Viral and Bacterial Pathogens".1. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture" MoL Cell Probes 3:375-382.
Lamoureux et al., 1997 "Detection of Campylobacter jejuni in Food and Poultry Viscera Using Immunomagnetic Separation and Microtitre Hybridization" J. Appl. Microbiol. 83:641-651.
Coutlee et al., 1990 "Quantitative Detection of Messenger RNA by Solution Hybridization and Enzyme Immunoassay" Biol. Chem. 265:11601-11604.
Stoller, B.D. and A. Rashtchian, 1987 "Immunochemical Approaches to Gene Probe Assays" Anal. Biochem. 161:387-394.
Blais, B.W., 1994 "Transcriptional Enhancement of the Listeria Monocytogenes PCR and Simple Immunoenzymatic Assay of the Product Using Anti-RNA:DNA Antibodies" AppL Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbiol. 27:120-125.
Boguslawski et al., 1986 "Characterization of Monoclonal Antibody to DNA:RNA and Its Application to Immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Colorimetric Fluorescent, and Enzymatic Amplification Substrate Systems in an Enzyme Immunoassay for Detection of DNA-RNA Hybrids" J. Clin. Microbiol. 27:1002-1007.
Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.
McLauchlan et al., DNA sequence homology between two co-linear loci on the HSV genome which have different transforming abilities, The EMBO Journal, 1983, vol. 2, No. 11, pp. 1953-1961.
Goldsborough et al., Nucleotide Sequence of Human Papillomavirus Type 31: A Cervical Neoplasia Associated Virus, Virology, 1989, vol. 171, pp. 306-311.
McGeoch et al., "DNA Sequence and Genetic Content of the Hindlll 1 Region in the Short Unique Component of the Herpes Simplex Virus Type 2 Genome; Identification of the Gene Encoding Glycoprotein G, and Evolutionary Comparisons," J. Gen. Virol., 1987, vol. 68, pp. 19-38.
McGeoch et al., The Complete DNA Sequence of the Long Unique Region in the Genome of Herpes Simplex Virus Type I, 1 Gen Virol., 1988, vol. 69, pp. 1531-1574.
Yamada et al., Human Papillomavirus Type 16 Variant Lineages in United States Populations Characterized by Nucleotide Sequence Analysis of the E6, L2, and Ll Coding Segments, J. Virol., Dec. 1995, vol. 69, No. 12, pp. 7743-7753.
Swain et al., Nucleotide Sequence of the Herpes Simplex Virus Type 2 Thymidine Kinase Gene, Virol., Jun. 1983, vol. 46, No. 3, pp. 1045-1050.
Delius et al., Primer-Directed Sequencing of Human Papillomavirus Types, Current Topics in Microbiology and Immunology, 1994, vol. 185, pp. 13-31.
Blair et al., Herpes Simplex Virus Virion Stimulatory Protein mRNA Leader Contains Sequence Elements Which Increase Both Virus-Induced Transcription and mRNA Stability, J. Virol., Aug. 1987, vol. 62, No. 2, pp. 444-453.
Larder et al., Related functional domains in virus DNA polymerases, The EMBO J., 1987, vol. 6, No. 1, pp. 169-175.
McGeoch et al., Structures of Herpes Simplex Virus Type 1 Genes Required for Replication of Virus DNA, J. Virol., vol. 62, No. 2, pp. 444-453.
Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.
International Search Report and Written Opinion based on PCT/US2001/037012 mailed Apr. 17, 2012.
Tungteakkhun et al., J. Virol., Feb. 2010, vol. 84, No. 3, pp. 1453-1463.
Qiagen Gaithersburg, Inc.; Determination of E6/7:E2 Transcript Ratios in Siha, Caski and Hela Cells; D15; March 1, 2011; pp. 1-5.
International Search Report Based on Application No. PCT/US2012/020684 Mailed October 25, 2012.
Clad et al.; "Performance of the Aptima High-Risk Human Papillomavirus MRNA Assay in a Referral Population in Comparison With Hybrid Capture 2 and Cytology"; Journal of Clinical Microbiology; March 2011; LNKD- Pubmed:21191046; vol. 49; No. 3; Dec. 29, 2010; pp. 1071-1076; Abstract.
Li et al; Detection of Human Papillomavirus Genotypes With Liquid Bead Microarray in Cervical Lesions of Northern Chinese Patients; Cancer Genetics and Cytogenetics, Science Publishing, New York, NY, US; vol. 182; No. 1; March 6, 2008; pp. 12-17; Abstract Elsevier.

(56) References Cited

OTHER PUBLICATIONS

Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; June 1, 2006; pp. 2025-2031; Abstract.

Han et al.; "Simultaneous Amplification and Identification of 25 Human Papillomavirus Types With Templex Technology"; Journal of Clinical Microbiology 200611 US LNKD- DOI:10.1128/JCM.01762-06; vol. 44; No. 11; Nov. 2006; pp. 4157-4162; Abstract.

Database EMBL [Online]; July 19, 2007; "Sequence 25 From Patent EP1806410"; XP002675256; Retrieved From EBI Accession No. EMBL:CS642417; Database Accession No. CS642417; The Whole Document.

Database EMBL [Online]; December 14, 2010; "Sequence 26 From now U.S. Pat. No. 7,812,144"; XP00267527; Retrieved From EBI Accession No. EMBL:GX640151; Database Accession No. GX640151; The Whole Document.

Database Geneseq [Online]; January 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.

Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.

Database Geneseq [Online]; Apr. 1, 2010; "HPV16 E7 Gene Forward RT-PCR Primer Seq ID 49"; XP002675260; Retrieved From EBI Accession No. GSN:AXU96631; Database Accession No. AXU96631; The Whole Document.

Database Geneseq [Online]; Apr. 21, 2005; "E7 Coding Region (1-87) Amplifying Sense PCR Primer, SEQ ID No: 37"; XP002675261; Retrieved From EBI Accession No. GSN:ADX15568; Database Accession No. ADX15568; Sequence.

Supplementary European Search Report based on Application No. 10 77 0411 mailed Oct. 29, 2012.

Stumph et al.; "Gene Enrichment Using Antibodies to DNA/RNA Hybrids: Purification and Mapping of Dictyostelium Discoideum RDNA"; Biochemistry; vol. 17; No. 26; Dec. 1, 1978; pp. 5791-5798.

Chinese First Action dated Apr. 15, 2013, issued in Application No. 201080018737.6 and English translation thereof.

Lowe et al; "A Hybrid-Capture Assay to Detect HPV MRNA Ratios in Cervical Specimens"; Journal of Virological Methods; Vol. 179; No. 1; January 2012; pp. 142-147.

International Search Report Based on Application No. PCT/US2012/026380 Mailed Oct. 15, 2012.

International Search Report and Written Opinion of the International Searching Authority Based on Application No. PCT/US2012/063385 Malied Feb. 5, 2013.

Schwalbe et al.; "Selective Reduction of the Interaction of Magnetic Nanoparticles With Leukocytes and Tumor Cells by Human Plasma"; Journal of Magnetism and Magnetic Materials, No. 1; May 1, 2005; pp. 433-437; Elsevier Science Publishers; Amsterdam, NL; vol. 293.

Coutlee et al., "Nonisotopic Detection of RNA in an Enzyme Immunoassay Using a Monoclonal Antibody against DNA-RNA Hybrids." Analytical Biochemistry 181, 153-162 (1989).

Luo et al., "Adiponectin stimulates human osteoblasts proliferation and differentiation via the MAPK signaling pathway," Experimental Cell Research, Academic Press, US, 309:1, (Sep. 10, 2005) 99-109, XP005037411.

Ouitas N. et al., "A Novel ex vivo skin model for the assessment of the potential transcutaneous anti-inflammatory effect of topically applied Harpagophytum procumbens extract," International Journal of Pharmaceutics, Elsevier BV, NL, 376: 1-2, (Jul. 6, 2009), 63-68, XP026185227.

Scholz et al., "Analysis of human immunodeficieny virus matrix domain replacements," Virology, Elsevier, Amsterdam, NL. 371: 2, (Nov. 8, 2007) 322-335, XP022439785.

Xie H. et al., "Apelin in and its receptor are expressed in human obsteoblasts," Regulatory Peptides, Elsevier Science B.V., NL, 134: 2-3, (May 15, 2006), 118-125, XP27895144.

Zhang W. et al., " Bone-Targeted Overespression of Bcl-2 Increases Osteoblast Adhesion and Differentiation and Inhibits of Mineralization In Vitro," Calcified Tissue International, Springer-Verlag, NE, 80: 2, (Feb. 2, 2007), 111-122.

European Office Action dated Jul. 14, 2014, issued in Application No. 10 755 291.1-1406.

European Office Action dated Jul. 4, 2014, issued in Application No. 09 752 940.8-1403.

Japanese Office Action dated Jun. 30, 2014, issued in Application No. 2011-548258.

Chinese Office Action dated May 4, 2014, issued in Application No. 200980143682.9, English translation.

International Preliminary Report on Patentability dated May 6, 2014, issued in Application No. PCT/US2012/063385, English translation.

English Translation of Second Chinese Office Action dated Jan. 31, 2013, issued in Application No. 201080018737.6.

\* cited by examiner

NON-TARGET AMPLIFICATION METHOD FOR DETECTION OF RNA SPLICE-FORMS IN A SAMPLE

CROSS-REFERENCE TO RELATED APPLICATIONS

This Non-Provisional patent application, filed under 35 U.S.C. §111(a), claims the benefit under 35 U.S.C. §119(e)(1) of U.S. Provisional Patent Application No. 61/174,938, filed under 35 U.S.C. §111(b) on 1 May 2009, and U.S. Provisional Patent Application No. 61/174,946, filed under 35 U.S.C. §111(b) on 1 May 2009, each of which is hereby incorporated by reference in its entirety.

BACKGROUND

1. Field

The present disclosure relates to methods and kits for determining the presence of ribonucleic acid (RNA) in a sample.

2. Description of Related Art

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations. Characterization of the RNA species involved in normal biological processes may be important to understanding various little known biological processes.

Detection

The detection and characterization of RNA (e.g., messenger RNA, transfer RNA, ribosomal RNA, small nuclear RNA, and other RNAs) is an important tool in many fields including molecular biology, toxicology, and biochemistry. Messenger RNA (mRNA) is an essential functional constituent of a cell; during the process of gene expression, the functional single strand structure of mRNA is synthesized and serves as an intermediate template for the translation process in protein synthesis. The brief existence of an mRNA molecule begins with transcription of DNA into an RNA molecule, and ultimately ends in degradation. During its life, an mRNA molecule may also be processed, edited, and transported prior to translation. Splicing is the process by which pre-mRNA is modified to remove certain stretches of non-coding sequences called introns; the stretches that remain may include protein-coding sequences and are called exons. Sometimes pre-mRNA messages may be spliced in several different ways, allowing a single transcript to encode multiple proteins.

Detection of messenger RNA (mRNA) is critical in diagnostics because it can provide viral load and gene expression information that DNA detection cannot. These factors often give clues about the progression and prognosis of a disease. The current technologies for mRNA detection present a number of problems including expense and potential for contamination.

Reverse hybrid capture is a novel non-target amplification method for RNA detection that can be used to detect specific gene transcripts from biological samples with a very low risk for contamination. This method uses DNA probes that are hybridized to the RNA targets. The created hybrids are then detected with a hybrid capture antibody system.

The most common methods of mRNA detection include Northern blot, ribonuclease protection assay (RPA), and reverse-transcriptase polymerase chain reaction (RT-PCR). However, each of these techniques, while affording some advantages in sensitivity, requires time and material demands. In addition, some techniques require amplification of the target mRNA since total mRNA represents only about 1% of the total RNA and any particular mRNA is a significantly smaller percentage.

Characterization

Currently, reverse transcriptase-polymerase chain reaction (RT-PCR) is widely used to characterize RNA transcripts. However the method has the following limitations: 1) only a limited number of the specific regions can be co-amplified; 2) mutations or alternative splicing can limit the ability of specific primers to detect the RNA; and 3) it is difficult to characterize the mRNA structure in a continuous mode method.

BRIEF SUMMARY

The present disclosure provides a non-target amplification method of RNA detection that is capable of characterizing RNA transcripts. In one embodiment, the present disclosure provides a non-target amplification method of mRNA detection that is capable of characterizing mRNA transcripts.

The present disclosure provides a method of detecting the presence of a target RNA, the method comprising: a) providing at least one DNA capture probe, wherein the at least one DNA capture probe is bound to a support; b) hybridizing the target RNA to said at least one DNA capture probe, yielding a target RNA:DNA capture probe complex; c) isolating the target RNA:DNA capture probe complex; d) providing at least one DNA amplification probe, and hybridizing said at least one DNA amplification probe to said target RNA:DNA capture probe complex, yielding a target RNA:DNA capture/amplification probe complex; e) providing an anti-RNA:DNA hybrid antibody, and incubating said target RNA:DNA capture/amplification probe complex with said antibody, yielding a target RNA:DNA:antibody complex; f) detecting said antibody, wherein said detecting indicates the presence of said target RNA. In one aspect, antibody is conjugated to a detectable marker, and the step of detecting comprises detecting the marker. In one aspect, the detectable marker is selected from the group consisting of alkaline phosphatase and horseradish peroxidase. In one aspect, the step of detecting comprises providing a second antibody that binds to said anti-RNA:DNA hybrid antibody, wherein said second antibody is conjugated to a detectable marker, and wherein said detecting further comprises detecting the marker. In one aspect, the support comprises a magnetic bead. In one aspect, the magnetic bead is conjugated to at least one streptavidin molecule, and the at least one DNA capture probe is conjugated to a biotin molecule.

The target RNA may be from virus, bacteria, mycobacteria or plasmodia. The target RNA may be from Herpesviridae, human immunodeficiency viruses, bacteriophages, *Chlamydia* spp., *Neisseria* spp., *Staphylococcus aureus*, mycobacteria, SARS coronavirus, Orthomixoviridae, or Papillomaviridae.

In one aspect, the at least one DNA capture probe and the at least one DNA amplification probe are from about 15 to about 200 bases in length.

In one aspect, the target RNA is a splice variant, and the at least one DNA capture probe and the at least one DNA amplification probe are selected to detect the presence of said splice variant.

In one aspect, the at least one DNA capture probe and the at least one DNA amplification probe are complementary to RNA from HPV high risk types 16, 18, 31, 33, 35, 39, 45, 51, 52, 56, 58, 59, 68, 26, 66, 73, and 82.

The present disclosure provides a kit for the detection of a target RNA, the kit comprising: a) at least one DNA capture probe, bound to a magnetic support; b) at least one DNA amplification probe; c) an anti-RNA:DNA hybrid antibody; and d) a detection reagent. In one aspect, said anti-RNA:DNA hybrid antibody is conjugated to a detectable marker, and said detection reagent comprises a substrate for said detectable marker. In one aspect, the kit further comprises a second antibody that binds to said anti-RNA:DNA hybrid antibody, wherein said second antibody is conjugated to a detectable marker, and wherein said detection reagent comprises a substrate for said detectable marker.

The present disclosure provides a method of providing target RNA for detection, the method comprising: incubating a biological sample containing the target RNA with carboxyl beads; isolating the beads; lysing the biological sample attached to the isolated beads; and isolating the beads from the lysed biological sample, wherein the resulting supernatant contains the target RNA for detection.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

In FIG. 13, each set of 5 oligos are adjacent to one another and result in the RNA:DNA hybrid getting longer, and signal stronger, as successive sets are added.

DETAILED DESCRIPTION

Figure 1:
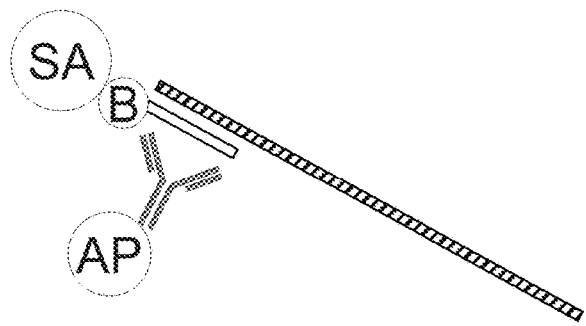
FIG. 1 is a schematic diagram of target RNA (crosshatched bar) captured by biotinylated DNA probes (white bar). "B" represents a biotin moiety; "SA" represents a streptavidin moiety; "AP" represents alkaline phosphatase conjugated to an antibody, but SA could be any other appropriate detectable moiety (e.g., horseradish peroxidase, etc.).

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

Methods of the present disclosure may be used to detect the presence of a target nucleic acid from samples. Such nucleic acid may be an RNA, and such samples may include, without limitation, a specimen or culture (e.g., cellular, microbiological and viral cultures) including biological and environmental samples. Biological samples may be from a eukaryote, a prokaryote, an archaeon, a virus, an animal, including a human, a plant, a fungus, an excavate, and may be from fluid, solid (e.g., stool) or tissue, cell culture, liquid or solid media, as well as liquid and solid food and feed products and ingredients such as dairy items, vegetables, meat and meat by-products, and waste. Environmental samples include environmental material such as surface matter, soil, water, air and industrial samples, as well as samples obtained from food and dairy processing instruments, apparatus, equipment, utensils, disposable and non-disposable items. Particularly preferred are biological samples including, but not limited to, cervical epithelial cells (e.g., a sample obtained from a cervical swab or biopsy), adenoid cells, anal epithelial cells, blood, saliva, cerebral spinal fluid, pleural fluid, milk, lymph, sputum and semen. The sample may comprise a ribonucleic acid including messenger RNA (mRNA).

The present disclosure provides a method for determining the presence of a target RNA in a sample, wherein the method comprises: a) hybridizing the target RNA with a DNA capture probe having a sequence complementary to the target RNA to form a target RNA:DNA capture probe complex, wherein the DNA capture probe is conjugated to a support; b) separating the target RNA:DNA capture probe complex from unbound RNA (e.g., by washing); c) optionally hybridizing at least one amplification probe to the target RNA:DNA capture probe complex, wherein the at least one amplification probe has a sequence complementary to the target RNA, thereby forming a target RNA:DNA capture/amplification probe complex; d) adding an antibody that recognizes and binds to RNA:DNA hybrids to bind the target RNA:DNA capture/amplification probe complex, thereby forming a target RNA:DNA:antibody complex, wherein the antibody is labeled with a detectable marker; e) detecting the marker on said antibody, wherein the detecting indicates the presence of the target ribonucleic acid; and f) comparing the detection results with results produced from a different combination of amplification probes wherein the comparing indicates the particular RNA splice-form present.

The present disclosure provides a method for determining the presence of a target RNA in a sample, wherein the method comprises: a) hybridizing the target RNA with a DNA capture probe having a sequence complementary to the target RNA to form a target RNA:DNA capture probe complex, wherein the DNA capture probe is conjugated to a support; b) separating the target RNA:DNA capture probe complex from unbound RNA; c) optionally hybridizing at least one amplification probe to the target RNA:DNA capture probe complex, wherein the at least one amplification probe has a sequence complementary to the target RNA, thereby forming a target RNA:DNA capture/amplification probe complex; d) adding an antibody that recognizes and binds to RNA:DNA hybrids to bind the target RNA:DNA capture/amplification probe complex, thereby forming a target RNA:DNA:antibody complex; e) adding a second antibody that recognizes and binds the first antibody, wherein the second antibody is labeled with a detectable marker; f) detecting the marker on the second antibody, wherein the detecting indicates the presence of the target ribonucleic acid; and g) comparing the detection results with results produced from a different combination of amplification probes wherein the comparing indicates the particular RNA splice-form present.

The present disclosure also provides a method of detecting the presence of a ribonucleic acid (RNA) splice form in a sample, wherein the method comprises a) hybridizing the target RNA with a DNA capture probe having a sequence complementary to the target RNA under conditions that allow the probe and the target ribonucleic acid to hybridize, thereby forming a target RNA:DNA capture probe complex; b) adding a first antibody that recognizes and binds to RNA:DNA hybrids to bind the target RNA:DNA capture probe complex, thereby forming a target RNA:DNA capture probe:antibody complex, wherein the first antibody is conjugated to a support; c) separating the target RNA:DNA capture probe:antibody complex from unbound RNA; d) hybridizing at least one amplification probe to the target RNA:DNA capture probe:antibody complex, wherein the at least one amplification probe has a sequence complementary to the target RNA and is added in a combination that will cover specific target RNA regions, thereby forming a target RNA:DNA:antibody complex; e) adding a second antibody that recognizes and binds to RNA:DNA duplexes to bind the target RNA:DNA:antibody complex, to form a target RNA:DNA:antibodies complex, wherein the second antibody is labeled with a detectable marker; f) detecting the marker on said second antibody, wherein the detecting indicates the presence of the target RNA; and g) comparing the detection results with results produced from a different combination of amplification probes wherein the comparing indicates the particular RNA splice-form present.

The present disclosure also provides a method of detecting the presence of a ribonucleic acid (RNA) splice form in a sample, wherein the method comprises a) hybridizing the target RNA with a DNA capture probe having a sequence complementary to the target RNA under conditions that allow the probe and the target ribonucleic acid to hybridize, thereby forming a target RNA:DNA capture probe complex; b) adding a first antibody that recognizes and binds to RNA:DNA hybrids to bind the target RNA:DNA capture probe complex, thereby forming a target RNA:DNA capture probe:antibody complex, wherein the first antibody is conjugated to a support; c) separating the target RNA:DNA capture probe:antibody complex from unbound RNA; d) hybridizing at least one amplification probe to the target RNA:DNA capture probe:antibody complex, wherein the at least one amplification probe has a sequence complementary to the target RNA and is added in a combination that will cover specific target RNA regions, thereby forming a target RNA:DNA:antibody complex; e) adding a second antibody that recognizes and binds to RNA:DNA duplexes to bind the target RNA:DNA:antibody complex, to form a target RNA: DNA:antibodies complex; f) separating the target RNA: DNA:antibodies complex from unbound second antibody; g) adding a third antibody labeled with a detectable marker wherein the third antibody recognizes and binds to the second and/or first antibody; h) detecting the marker on the third antibody, wherein the detecting indicates the presence of the target RNA; and i) comparing the detection results with results produced from a different combination of at least one amplification probe wherein the comparing indicates the RNA splice-form present.

RNA is often transcribed from different promoters, thereby generating multiple forms that include the coding regions for different genes. It is important to characterize these multiple spliced forms of RNA for fundamental research and for applications where the detection of specific mRNA isoforms is critical.

One application of the present disclosure is the detection and characterization of mRNA expression in human papillomavirus (HPV). Carcinoma of the cervix has been shown to be associated with the presence of high-risk HPV types; from about 13 to about 18 high-risk types are currently identified. The HPV DNA test can identify high-risk HPV types, but is a poor predictor for the progression of the disease in pre-cancerous clinical specimens. Thus, additional methods and markers are needed to improve the predictive value of HPV tests. The characterization of mRNA for the presence of the E6/7 oncogene and other mRNAs, as provided by the present disclosure, will allow an accurate and reliable method that determines the ratio of expression of these oncogenes versus other viral genes. The ratio of E6/E7 to E2, E4, and/or L1 mRNA may be a better predictor for the progression of precancerous cervical lesions (see, e.g., U.S. Pat. No. 6,355,424, incorporated by reference herein), yet currently-available assays do not detect mRNA ratios. Hybrid capture technology is a linear signal amplification method. Thus, the instant disclosure provides valuable methods for guiding therapeutic strategy, while minimizing the number of patients requiring colposcopy. The instant disclosure provides methods of using mixtures of short oligonucleotides capable of hybridizing to the different lengths/genes of RNA (and mRNA in particular) in order to characterize splice forms.

Target Nucleic Acids

In one embodiment, the target ribonucleic acid to be detected may be mRNA, ribosomal RNA, nucleolar RNA, transfer RNA, viral RNA, heterogeneous nuclear RNA etc., wherein the one or more polynucleotide probes are DNA probes. The target ribonucleic acids include, without limitation, nucleic acids found in specimens or cultures (e.g., cellular, microbiological and viral cultures) including biological and environmental samples. The target ribonucleic acids may be found in biological samples from an animal, including a human, fluid, solid (e.g., stool) or tissue, as well as liquid and solid food and feed products and ingredients such as dairy items, vegetables, meat and meat by-products, and waste. Target ribonucleic acids may be found in environmental samples and include environmental material such as surface matter, soil, water and industrial samples, as well as samples obtained from food and dairy processing instruments, apparatus, equipment, utensils, disposable and non-disposable items. Particularly preferred are target nucleic acids found in biological samples including, but not limited to cervical samples (e.g., a sample obtained from a cervical swab), adenoid cells, anal epithelial cells, blood, saliva, cerebral spinal fluid, pleural fluid, milk, lymph, sputum, urine and semen.

In other embodiments, the target ribonucleic acids are from virus, bacteria, mycobacteria or plasmodia, for example, without intending to be limited thereby, cytomegalovirus (CMV), Herpesviridae, human immunodeficiency virus (HIV), *Chlamydia* spp., *Neisseria* spp. (e.g.; *N. gonorrhea*), *Staphylococcus aureus*, mycobacteria (e.g., Mycobacterium tuberculosis), SARS coronavirus (SARS-CoV), or Orthomixoviridae (e.g., influenza viruses).

In one embodiment, the target ribonucleic acids are human papillomavirus (HPV) and include genetic variants of HPV. A variant includes polymorphisms, mutants, derivatives, modified, altered, or the like forms of the target nucleic acid. In one embodiment, the target nucleic acid is an HPV nucleic acid. In another embodiment, the HPV nucleic acid is HPV DNA of a high risk HPV type. In another embodiment the target nucleic acids are high risk HPV types 16, 18, 31, 33, 35, 39, 45, 51, 52, 56, 58, 59, 68, 26, 66, 73, and 82.

The RNA may be isolated and prepared for hybridization by a variety of methods and reagents including (but not limited to) guanidinium thiocyanate-phenol-chloroform extraction (e.g., with TRIzor reagent, also known as TRI Reagent), hypotonic lysis, and carboxyl (COOH) bead capture. The principle of RNA isolation is based on cell/tissue lysis, followed by extraction, precipitation, and washing. While very effective, these techniques require a high level of technical precision and are not candidates for automation. Other RNA preparation methods do not completely eliminate DNA and other potential contaminants, require expensive enzymes, and require many—sometimes time-consuming—washing steps. The challenge is to develop a method for mRNA detection that reduces many of the current challenges and can provide rapid information about expression of specific genes. Two primary sample preparation methods have been devised for the present disclosure: hypotonic cell lysis; and carboxyl bead capture. RNA isolated using TRIzol® or QIAGEN resin technology (for example, QIAGEN RNeasy Plus Mini Kit) can also be used in this assay.

In certain embodiments, the biological sample is comprised of cervical cells, especially human cervical cells. The sample can be collected with any method or device known in the art, including a chemically inert collection device such as a Dacron® (poly(ethylene terephthalate)) tipped swab. Other acceptable collection devices may be used including, but not limited, to cotton swab, cervical brush, flocked swab (a swab shaped like a Dacron® swab but made with nylon fibers enabling collection of more cells and easier release of cells), cervical broom, mini broom, lavage, or any collection device often used in PAP smear testing (Papanikolaou's test). The cervical cells may also be part of a biopsy specimen.

Sample Preparation

Figure 5:
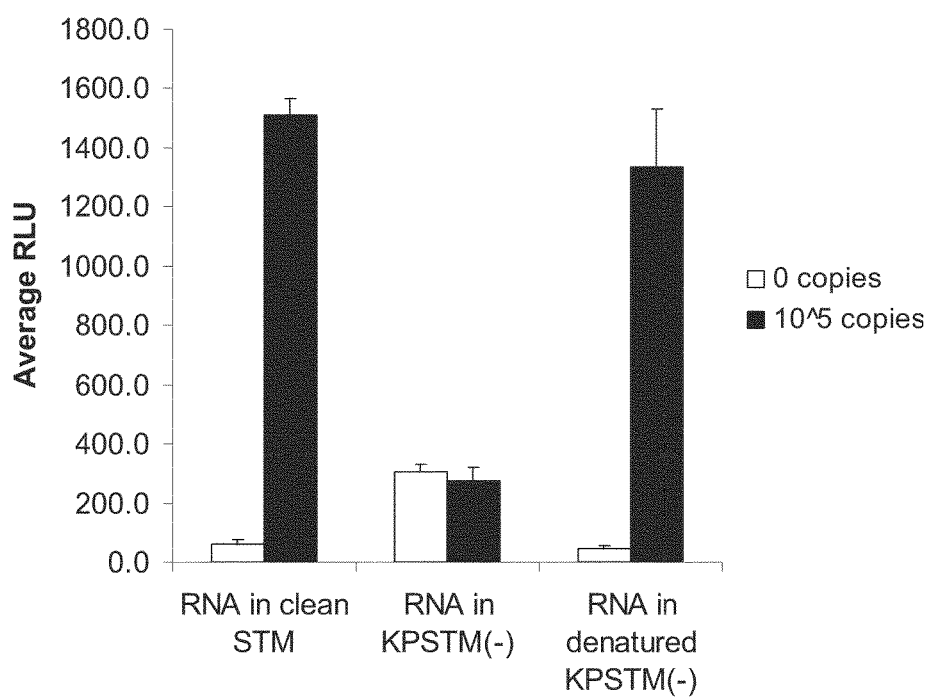
FIG. 5 shows that endogenous hybrids are often the source of clinical background noise. "RLU"=relative luminescence unit.
Figure 6:
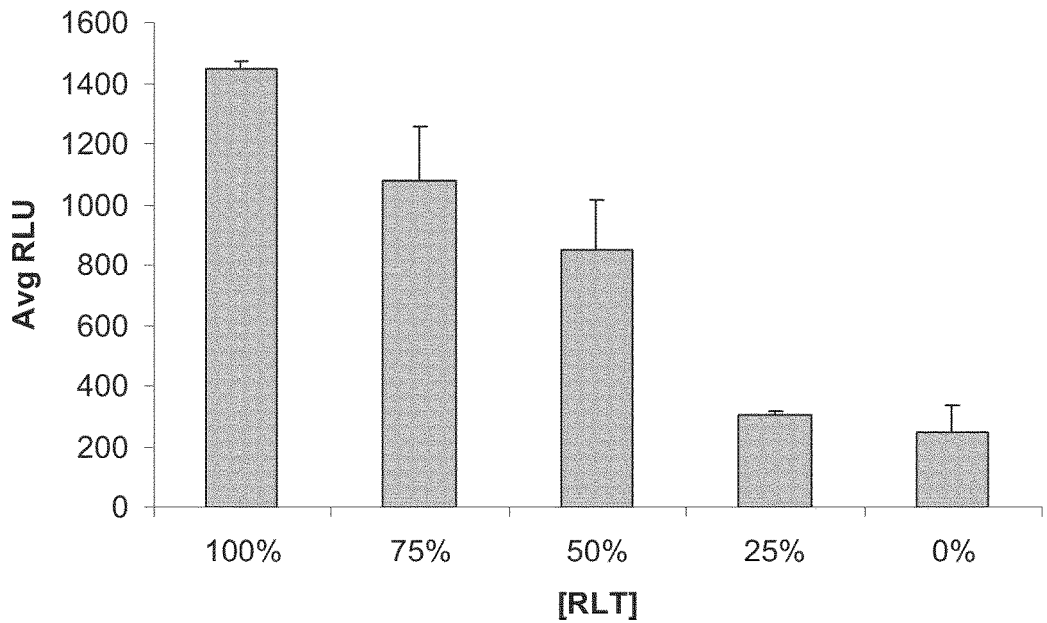
FIG. 6 shows the effect of lysis buffer (wherein 100% buffer contains about 3 M guanidine thiocyanate and about 2% detergent) concentration on assay background when assaying cellular samples in PreservCyt® Solution, and demonstrates that clinical background decreases with decreasing concentrations of lysis buffer.

The use of TRIzol® to isolate RNA, as well as other known methods for RNA isolation, may be employed in methods of the present disclosure. Sample preparation by hypotonic lysis of the cell pellet avoids releasing endogenous RNA:DNA hybrids that may interfere with assay detection step, and this is a preferable RNA isolation method. In this sample preparation method, cells are pelleted via centrifuge, the supernatant is removed, and the pellet is resuspended and the cells lysed. After lysis, the cellular debris is pelleted and the supernatant (containing RNA)

collected. Reducing the stringency of lysis (as measured by salt and detergent concentrations in a buffer) reduces the clinical background produced from pools of methanol-based cervical specimens (FIGS. 5 & 6). The signal:noise ratios are also higher and the variability in background between pools and in interference is lower. Other studies have shown that hypotonic lysis works by rupturing the cellular membrane because of differences in tonicity between the cell and the milieu, but organelles are left intact. Thus, RNA in the cell is released from the cell into the solution, whereas contaminants to the assay (such as endogenous RNA:DNA hybrids) will remain in the insoluble cell debris. This method may be useful in cases where the amount of RNA in a specimen is limited because increasing the amount of specimen does not lead to an increase in background.

Another method of sample preparation uses magnetic carboxyl (COOH) beads that can be added directly to a biological sample. Cells in the sample are attracted to the beads via hydrophobic interactions. After using a magnetic rack to pellet the beads, the supernatant can be removed and the cells lysed. Non-magnetic COOH beads or other adsorbtive particles could also be used, substituting centrifugation for pelleting via a magnetic rack. After the lysis (which usually occurs at 65° C. for 15 min) the beads are again pelleted and the remaining supernatant may be used directly in methods of the present disclosure. While decreasing lysis stringency again reduces background in this method, water alone is not enough to release the RNA from the cells. As such, it is preferable to use a lysis buffer comprising about 1 M guanidine thiocyanate and about 0.7% detergent for all sample preparation methods of the present disclosure (see, e.g., FIGS. 5 & 6).

Hybridization/Capture—Capture Probes

Figure 3:
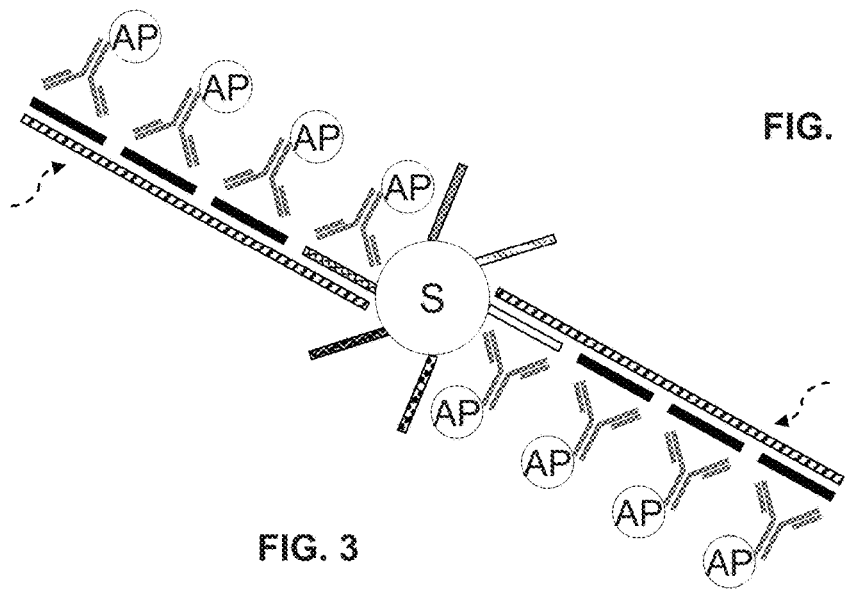
FIG. 3 is a diagram of target RNAs (dashed arrows) captured by different DNA capture probes bound to a substrate (S). Non-conjugated DNA amplification probes (black bars) and multiple antibodies that detect and bind to DNA:RNA hybrid regions (conjugated to alkaline phosphatase or any other appropriate detectable moiety, such as horseradish peroxidase, etc.) are also shown. The substrate (e.g., a bead) may bear multiple DNA capture probes, and the DNA capture probes may be the same (i.e., the same sequence and/or length) or different (i.e., different sequences and/or different lengths).
Figure 4:
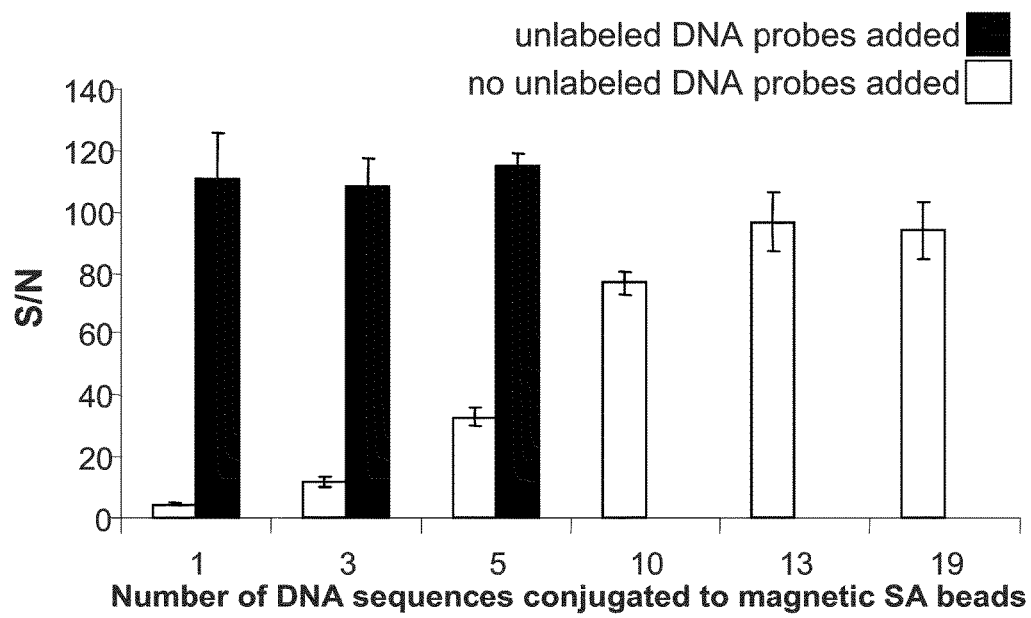
FIG. 4 provides the results of an experiment showing the effect of adding unbiotinylated DNA probes after RNA capture in this experiment, a variable number of biotinylated probes were conjugated to streptavidin beads. The target was the E6/7 gene transcript of HPV 16. The assay was performed with each set of beads with (black bars) and without (white bars) the addition of unlabeled signal amplification probes (one-versus two-step assay). When no signal amplification step was added (white bars), the signal increased with the amount of coverage provided by the capture probes. However, when signal amplification probes were added (black bars), the signal was much higher than in the one-step assay and only 3-5 capture probes were required for improved signal.

After the sample is prepared and target RNA is released, it is contacted with at least one polynucleotide DNA capture probe under a condition sufficient for the at least one polynucleotide probe to hybridize to the target RNA in the sample to form a double-stranded nucleic acid hybrid. The DNA capture probes may be full length, truncated, or synthetic DNA. The DNA capture probes are sequence specific for the target RNA. DNA capture probes are ideally about 35 bases long and may be complementary to any region of the target RNA. The DNA capture probes may range from about 15 to about 200 bases in length. The DNA capture probes can be bound to a support. "Bound" includes but is not limited to chemically attached, covalently bound, and covalently linked. Multiple DNA capture probes, and multiple different DNA capture probes may be bound to the same support (e.g., the same magnetic bead), as shown schematically in FIG. 3. Only 3-5 different capture probes are required for optimal results (see FIG. 4), thus providing a great deal of flexibility to allow these probes to be sequence-specific and not fall in regions that may be spliced out in some variants. In one embodiment, the sequence-specific DNA capture probes are biotinylated and have been bound by conjugation to magnetic streptavidin beads.

In one aspect, the present disclosure can optionally include the use of a set of DNA capture probes useful for detection of high risk (HR) human papillomaviruses, wherein the set comprises polynucleotide capture probes for HPV high risk types 16, 18, 31, 33, 35, 39, 45, 51, 52, 56, 58, 59, 68, 26, 66, 73, and 82.

Supports include, but are not limited to beads, magnetic beads, columns, plates, filter paper, polydimethylsiloxane (PDMS), and dipsticks. Any support can be used as long as it allows extraction of the liquid phase and provides the ability to separate out bound and unbound capture probes or antibodies. Magnetic beads are particularly useful in that they can be left in the solution and the liquid phase can be extracted or decanted, if a magnetic field is applied to hold the beads in place. Beads that are small and have a high surface area are preferable, such as beads about 1 μm in diameter. In certain embodiments, the support comprises a modified magnetic bead, that is coated or has attached thereto a DNA capture probe complementary and specific to the target mRNA. A magnetic field is used to separate the double-stranded nucleic acid/magnetic bead complex from non-bound ribonucleic acid. In certain embodiments, the support comprises a modified magnetic bead, wherein the magnetic beads are modified by coating the beads with a first antibody immunospecific for double-stranded hybrid nucleic acids. A magnetic field is used to separate the nucleic acid hybrid/antibody/magnetic bead complex from unbound ribonucleic acid. Other beads that employ charge switching or silica capture (as opposed to magnetic fields) may be used as well.

Following capture of the target RNA or the target RNA: DNA hybrid as described above, the captured target RNA or RNA:DNA hybrid may be separated from the rest of the sample by application of a magnetic field (in the case of magnetic beads), and washing away of non-captured nucleic acids. Washing away unwanted interfering substances may be accomplished with buffers Containing salt and or detergent that are used at various temperatures. When using supports other than magnetic beads, alternative methods of separating captured hybrid from the rest of the sample are conducted, including but not limited to, washing.

Hybridization/Capture—Amplification Probes

After the wash step to ensure that only the target remains, signal amplification DNA probes are hybridized to the target mRNA, wherein the signal amplification probes are unlabeled DNA probes complementary and/or specific to the target mRNA. The amplification probe need not be specific to the target nucleic acid. For example, the DNA amplification probe may be able to bind other nucleic acids other than the designed target. The DNA signal amplification probes complementary to the mRNA regions are designed and combined in mixtures that will cover specific genes. By extending and varying the coverage, one can determine which genes are present and the particular splice forms of the RNA. "Coverage" is defined as the extent or length of target sequence which is flanked by the complementary signal probes. The signal amplification probes are roughly 40 bases in length, but because they are designed around the capture probes, some may be more or less than 40 bases. Signal amplification probes may be about 15 to about 200 bases in length. Increasing coverage (i.e., hybridizing more signal probes to complementary regions of the target RNA) will lead to an increase in signal. Therefore, it is preferable to use more probes to obtain an amplified signal. The limit of detection depends, in part, on the length of the target nucleic acid (i.e., the target gene).

Amplification signal probes are added in combinations which would extend over the genetic sequence of known RNA splice-forms. The combination of signal amplification probes will determine the extent of coverage on the target mRNA and hence, signal output. Comparison of the resulting signal output from different combinations of amplification probes will indicate the presence of particular mRNA splice-form variants. In this way, this method is a "molecular ruler" in that the signal output is dependent on the splice form present. For example, capture probe 3 is expected to hybridize with E6/7 target mRNA, but not with E1, E2, E4, E5, L1, or L2 (see, e.g., TABLE 3 and FIG. 11). Signal amplification probes 1 and 6, used after hybridization with capture probe 3, will generate a strong signal from the spliced E6/7 form, and a weak signal from the spliced/integrated E6/7 form. By varying the combinations and numbers of capture probes and amplification probes, the signal output provides information about which viral genes are being expressed (e.g., the ratio thereof), as well as which splice forms of those genes are expressed. Such information, coupled with clinical and experimental data, is expected to provide a better predictor for progression of precancerous cervical lesions.

The characterization of gene expression in cells via measurement of mRNA levels is a useful tool in determining whether cells are infected with a pathogen, and the state of disease progression.

The present disclosure provides a method of determining lengths of gene transcripts for known and unknown splice form variants. A reliable and robust method for measuring the expression of alternatively spliced transcripts is an important step in investigating the significance of each variant. So far, accurate quantification of splice variants, such as Northern blotting, RT-PCR and real time RT-PCR, has been laborious and difficult due to the intrinsic limitations of conventional methods. The present disclosure provides methods of determining the presence of splice form variants. For example, the question of whether an early HPV transcript (for example HPV E6*I) bears late-gene sequences may be determined by capturing the transcript with capture probes complimentary to the early region, then detecting with detection probes that are complementary to the late region; resulting signal may indicate the presence of late regions on early gene transcripts. Furthermore, by providing a combination of degenerate signal amplification probes that would cover predicted splice form sequences, the presence of a splice variant could be determined. Furthermore, the absence of a region may be indicated by lack of capture by select DNA probes.

The resulting hybrids are captured/detected using molecules that recognize RNA:DNA hybrids. Molecules specific for the double stranded nucleic acid hybrids include, but are not limited to, monoclonal antibodies, polyclonal antibodies, proteins such as but not limited to RNAse H, nucleic acids including but not limited to aptamers, or sequence specific nucleic acids. Aptamers are short oligonucleotide or peptide molecules that bind to a particular target molecule. They are often created by selecting them from large pools of random sequences, although naturally-occurring aptamers (e.g., riboswitch aptamers) are known.

Hybridization/Capture—Anti-Hybrid Antibody

In one embodiment the molecule specific for the double stranded nucleic acid hybrid is an antibody ("anti-hybrid antibody"). The hybrids are incubated with the anti-hybrid antibody for a sufficient amount of time to allow binding to the double-stranded nucleic acid hybrids. The anti-hybrid antibody may be monoclonal or polyclonal. In a most preferred embodiment the antibody is monoclonal.

In another embodiment, the first antibody is bound to a support. In this embodiment, after the sample is prepared and RNA is released, it is contacted with at least one polynucleotide DNA capture probe under conditions sufficient for the at least one polynucleotide probe to hybridize to the target RNA in the sample to form a double-stranded nucleic acid hybrid. The target RNA, in the form of a target RNA:DNA capture probe complex is separated from unbound RNA by washing. After the wash step to ensure that the only RNA remaining is target RNA, signal amplification DNA probes are hybridized to the target RNA, wherein the signal amplification probes are unlabeled DNA probes that are complementary and/or specific to the target RNA. The hybridization of capture and amplification probes to the target RNA creates double stranded nucleic acid hybrids. The resulting hybrids are detected using molecules that recognize RNA:DNA hybrids. In a preferred embodiment the molecule specific for the double stranded nucleic acid hybrid is an antibody ("anti-hybrid antibody"). The hybrids are incubated with the anti-hybrid antibody for a sufficient amount of time to allow binding to the double-stranded nucleic acid hybrid regions. The anti-hybrid antibody is conjugated to a support and binding to the RNA:DNA hybrids forms an RNA:DNA hybrid:antibody complex. The complex is separated from unbound antibody. In applications where the support is a magnetic bead, a magnetic field is used to separate out any unbound antibody.

Detection

After unbound anti-hybrid antibody is removed, a second antibody is added, wherein the second antibody is labeled with a detectable marker and recognizes and binds to the first antibody. The label present on the second antibody is detected to thus indicate the presence of the target ribonucleic acid. Methods for detecting various labels are known in the art. For example, colorimetry, radioactive, surface plasmon resonance, or chemiluminescence methods are described by e.g., Coutlee, et al., J. Clin. Microbiol. 27:1002-1007 (1989).

For example, antibodies conjugated with at least one alkaline phosphatase molecule can be detected by chemiluminescence with a reagent such as a Lumi-Phos™ 530 reagent (Lumigen, Detroit, M1) or DR2 (Applied Biosystems, Foster City, Calif.) using a detector such as an E/Lumina™ luminometer (Source Scientific Systems, Inc., Garden Grove, Calif.), an Optocomp I™ Luminometer (MGM Instruments, Hamden, Conn.), or the like. As described herein, detection of the label on the second antibody is indicative of the presence of one or more of the target ribonucleic acids in the sample that are complementary to the one or more probes. Following washing, the sample is suspended in a detection buffer that for example, contains the substrate for the label on the second antibody.

Anti-hybrid antibodies can be used and/or coupled to magnetic beads and/or immobilized on a support in the present assay as described below. In a preferred embodiment, the antibodies used for capture and detection of the target nucleic acid are monoclonal antibodies. The first and second antibodies may be the same for capture and detection (i.e., produced by the same hybrid myeloma cell line) or may from different and produced by different hybrid myeloma cell lines. In a most preferred embodiment, the first and second monoclonal antibodies used for capture and/or detection are the same and are specific for RNA/DNA hybrids. Also included are immunofragments or derivatives of antibodies specific for double-stranded hybrids, where such fragments or derivatives contain binding regions of the antibody.

For example, a monoclonal RNA:DNA hybrid antibody derived from myeloma cells fused to spleen cells that are immunized with an RNA:DNA hybrid can be used. The hybrid-specific antibody can be purified by affinity purification against RNA:DNA hybrids immobilized on a solid support, for example as described in Kitawaga et al., Mol. Immunology, 19:413 (1982); and U.S. Pat. No. 4,732,847, each of which is incorporated herein by reference.

Other suitable methods of producing or isolating antibodies, including human or artificial antibodies, can be used, including, for example, methods that select recombinant antibody (e.g., single chain Fv or Fab, or other fragments thereof) from a library, or which rely upon immunization of transgenic animals (e.g., mice) capable of producing a repertoire of human antibodies (see, e.g., Jakobovits et al, Proc. Natl. Acad. Sci. USA, 90:2551 (1993); Jakobovits et al., Nature, 362: 255 (1993); and U.S. Pat. Nos. 5,545,806 and 5,545,807).

In yet another aspect, the present disclosure provides kits that allow for the detection of ribonucleic acids in a biological sample or a sample containing nucleic acids. In a preferred embodiment, the kit comprises a) a DNA capture probe conjugated to a magnetic bead; b) a DNA amplification probe; c) a first anti-hybrid antibody; d) a detection reagent comprising a second antibody, wherein the second antibody binds the first antibody and is detectably labeled; e) a detergent-based wash buffer and; f) a second detection reagent comprising a substrate for the label on the second antibody. A preferred detergent-based wash buffer is 40 mM Tris-HCl, 100 mM NaCl, 0.5% Triton X-100.

Figure 2:
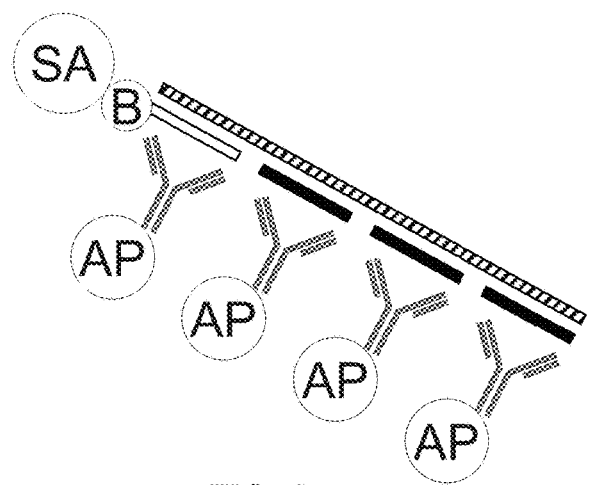
FIG. 2 is a diagram depicting the use of DNA capture probe (white bar), multiple DNA amplification probes (black bars), and multiple DNA:RNA hybrid antibodies to "amplify" the signal without the need for amplification of the target RNA (crosshatched bar). "B" represents a biotin moiety; "SA" represents a streptavidin moiety, B and SA may be replaced with other conjugation technology in which DNA probes are conjugated to the bead; "AP" represents alkaline phosphatase conjugated to an antibody, but AP could be any other appropriate detectable moiety (e.g., horseradish peroxidase, etc.).

In certain embodiments, detection methods of the present disclosure detect RNA by first capturing the target onto complementary biotinylated DNA probes that are conjugated to magnetic streptavidin beads: This probe-bead complex may be preconjugated and is stable at 4° C. for several months. This capture step is preferably performed at 60° C. with constant shaking and allowed to proceed for about 30 minutes (a time sufficient to allow capture). The beads with the captured target are then washed so that any non-target RNA sequences are removed. Because the hybrid capture antibody binds to individual DNA-RNA hybrids, it is preferable to cover the target region with DNA amplification probes to achieve the maximal signal (see FIGS. 1 & 2). Thus, additional probes are then hybridized to the target mRNA. Because only the target is captured at this point, these probes need not be sequence-specific but rather may cover the full length of the gene, excluding regions that are already covered by the biotinylated specific probes. The signal amplification probes are complementary to the mRNA regions and are designed and combined in mixtures that will cover specific genes. By extending and varying the coverage, particular genes and particular splice variants can be determined. These "signal amplification" probes are preferably used at concentration of 4.2 nM. This hybridization also preferably occurs at 60° C. for 30 min at a pH of around 7.8. The hybridization is then followed by detection with the hybrid capture antibody system discussed above (use of anti-hybrid antibody and a second antibody to detect the anti-hybrid antibody).

Example 1

Sample Preparation Via Hypotonic Lysis of Cell Pellet

Figure 7:
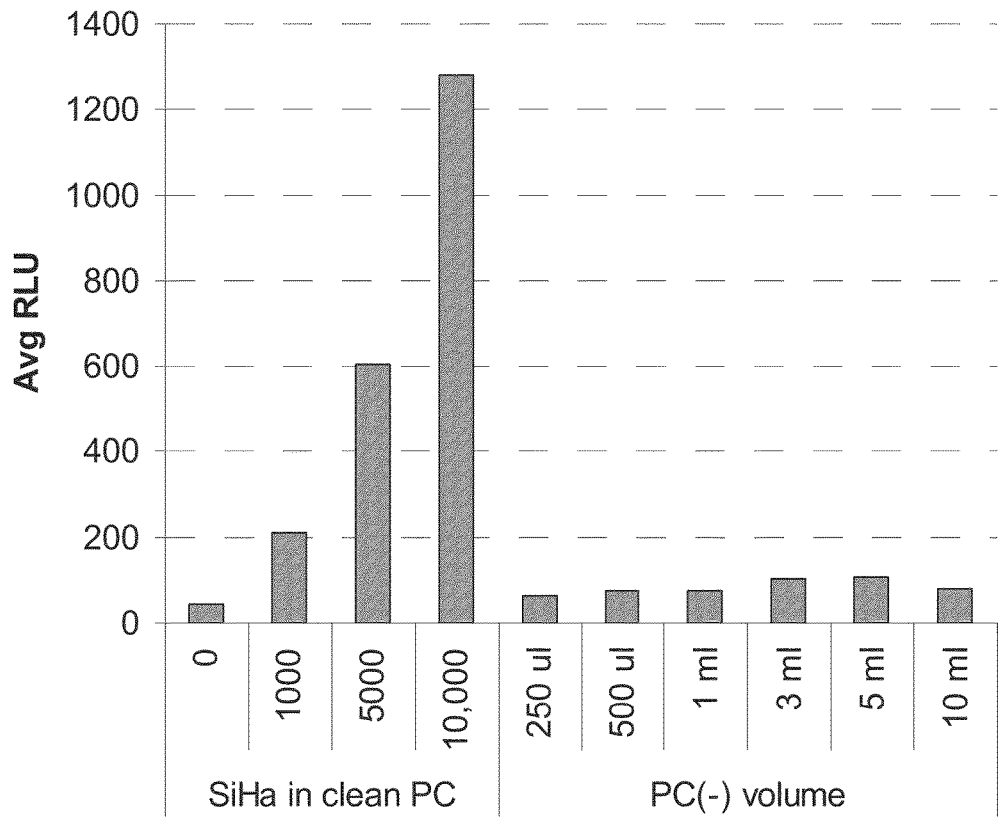
FIG. 7 shows that hypotonic lysis of cell pellets ensures that background noise remains stable and that the background does not change significantly regardless of the amount of specimen used. "PC"=PreservCyt® Solution; "PC(-)"=Specimen (cervical scrape) pool fixed in PreservCyt® Solution with no HPV target.
Figure 8:
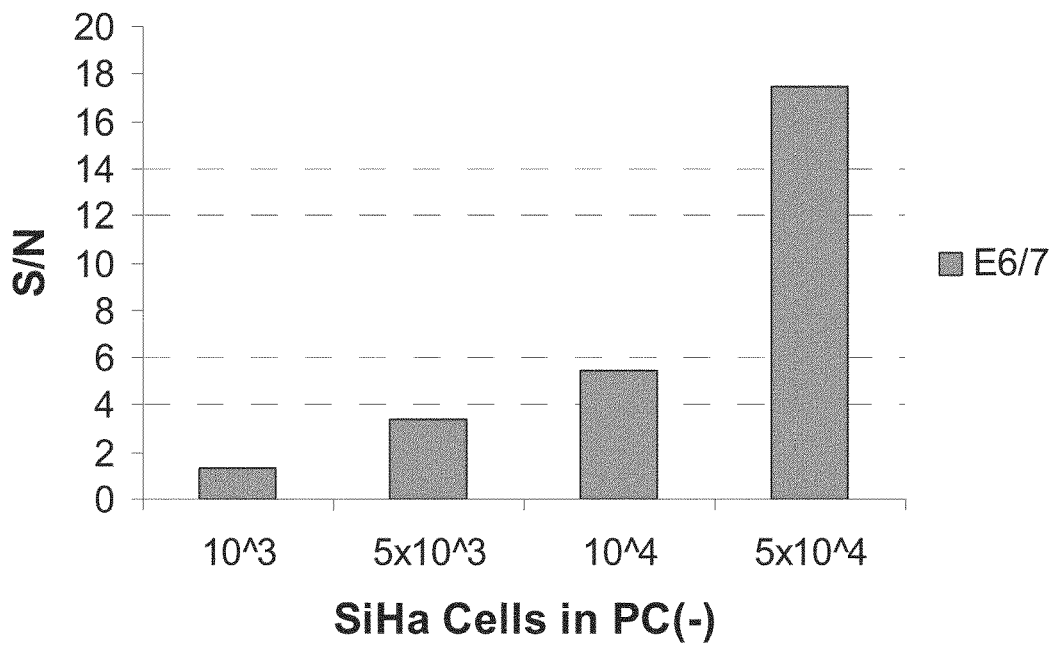
FIG. 8 shows limit of detection of HPV E6/E7 from HPV positive cells (SiHa). This shows that using the methods of the present disclosure, as little as $1\times10^3$ cells are required for HPV E6/7 RNA detection.

Endogenous hybrids present a unique challenge to detection assays because they will be detected by the hybrid capture antibody. Thus, sample preparation preferably either destroys or avoids releasing these hybrids. Hypotonic lysis relies on the latter strategy. In this method, cells are pelleted via centrifuge, the supernatant is removed, and the pellet is lysed. As is shown in FIG. 6, reducing the stringency of lysis by varying salt and detergent concentrations in a buffer reduces the clinical background produced from pools of methanol-based cervical specimens. The signal:noise ratios are also higher and the variability in background between pools and in interference is lower (TABLE 2). Other studies have shown that hypotonic lysis works by rupturing the cellular membrane because of differences in cellular tonicity compared to the milieu, but organelles are left intact. Thus, RNA in the cell is released from the cell into solution, whereas contaminants to the assay such as hybrids will remain with the insoluble cell debris. This method may be useful in cases where the amount of RNA in a specimen is limited because increasing the amount of specimen does not lead to an increase in background (FIG. 7). Using a model of spiking HPV positive cells into pools of negative cervical specimens, hypotonic lysis followed by detection methods of the present disclosure can detect HPV E6/7 RNA from just 1000 cells (FIG. 8).

Example 2

Sample Preparation Via Magnetic Carboxyl Beads

Figure 10:
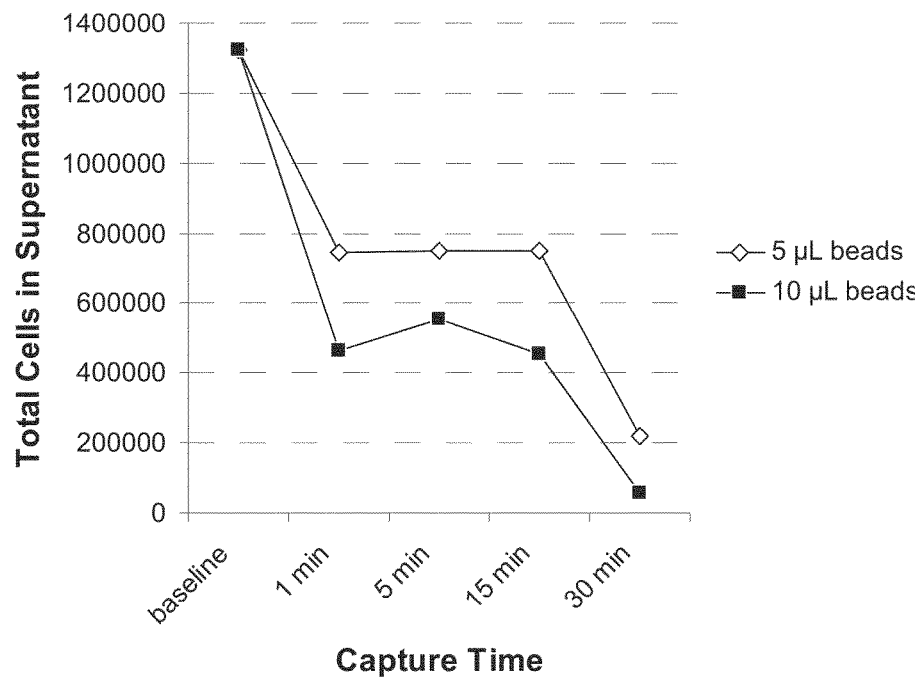
FIG. 10 shows cell capture by magnetic carboxylate-modified (COOH) beads (Sera Dyn catalog number 6515-2105-050350), over time, demonstrating that about 95% of the cells have been captured after incubation of 30 minutes.
Figure 11:
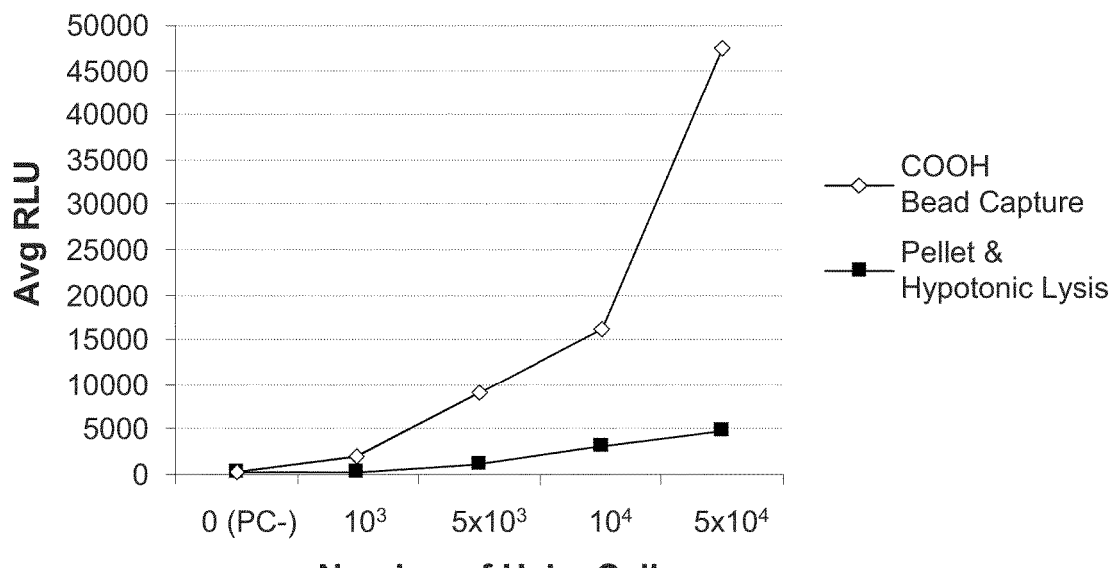
FIG. 11 shows comparison of COOH bead capture with hyotonic lysis, and indicates that COOH bead capture is more efficient than hypotonic lysis for obtaining mRNA from cells. "PC-" indicates a pool of cervical scrape specimens that lack presence of HPV.

Another sample preparation method that has been characterized for use in the methods of the present disclosure uses magnetic carboxyl modified (COOH) beads that can be added directly to a biological sample (e.g., Sera-Mag® Magnetic Carboxylate-Modified Particles; Thermo Fisher Scientific, Inc.). Cells in the sample are attracted to the beads via hydrophobic interactions. After using a magnetic rack to pellet the beads, the supernatant can be removed and the cells lysed. After lysis, the beads are again pelleted and the remaining supernatant is transferred for use in methods of the present disclosure. While decreasing lysis stringency again reduces background in this method (see TABLE 1), water alone is insufficient to release RNA from the cells. Rather, a preferred lysis buffer is about 1 M guanidine thiocyanate and about 0.7% detergent (see FIG. 9), as it supports both lysis and hybridization. Stronger lysis buffer concentrations may be used if it is diluted before the hybridization capture step. As shown in FIG. 10, the capture of cells onto the beads is a biphasic reaction. Carboxyl beads were spiked directly into PreseryCyt®-based samples of cervical cells. Approximately 50-60% of all the cells in the samples were attracted to the beads within the first minute of exposure. This process plateaus for at least 15 min, but approximately 30 min after adding the beads at least 95% of the cells have been captured (as measured by counting cells remaining in the supernatant; see FIG. 10). FIG. 11 shows that using methods of the present disclosure results could be obtained using only approximately 1000 HPV positive cells; carboxyl bead cell capture, followed by detection methods of the present disclosure, is more efficient at obtaining mRNA from cells than hypotonic cell lysis followed by detection methods of the present disclosure (see FIG. 11).

TABLE 1

| % Lysis Buffer | S/N |
|---|---|
| 100 | 1.6 |
| 50 | 3.2 |
| 32.5 | 7.0 |
| 25 | 1.7 |
| 0 | 0.9 |

Example 4

Effects of Endogenous Hybrids on Assay Background

Endogenous hybrids are often the source of clinical background noise (see FIG. 5). When HPV 16 E6/7 RNA is spiked into clinical pools (with no HPV; KPSTM(−)), the background is high and the signal is masked. However, when the pools are denatured (1.75 M NaOH) and neutralized before the RNA addition, the background is low and the signal is rescued. This reveals the need to eliminate or prevent release of endogenous nucleic acid hybrids before utilizing a detection method that employs antibodies that recognize nucleic acid hybrids.

Example 5

Effect of Lysis Buffer Concentration on Background

Reducing lysis stringency reduces clinical background noise (see FIG. 6). One mL of methanol-based cervical specimens were spun down and the pellets resuspended in buffer at various concentrations (100% buffer=about 3 M guanidine thiocyanate+about 2% detergent), as shown along the x-axis. Pelleted cells were heated for 15 min at 65° C. The final concentration of lysis buffer was then adjusted to 32.5% for the capture of RNA according to methods of the present disclosure. As shown in FIG. 6, the background decreased with decreasing concentrations of lysis buffer. This experiment provides evidence that hypotonic lysis of cells was successful in preventing release of endogenous nucleic acid hybrids. RNA in the cytoplasm is released from the cell whereas contaminants to the assay such as hybrids will remain in the nucleus.

In addition, water lysis gives lower background and variability and higher signal:noise than more stringent lysis (see TABLE 2, below). Values in TABLE 2 are averaged across results from four different clinical pools of cervical specimens. Typically, these pools vary greatly in background.

TABLE 2

| Lysis Condition | Background (RLUs) 1 mL PC-pools | Background Variability | S/N Ratio ($10^4$ SiHa Cells) |
|---|---|---|---|
| Water | 71 | 21.8% | 6.6 |
| 100% Lysis Buffer | 652.3 | 53.2% | 4.7 |

Example 6

Hypotonic Lysis of Cell Pellets

FIG. 7 shows that hypotonic lysis of cell pellets ensures that background noise remains stable. Varying amounts of cervical specimens (250 ul-10 ml) were spun down, lysed with water, and subjected to RNA detection assays of the present disclosure. As shown in the graph in FIG. 7, the background does not change significantly regardless of the amount of specimen used.

Example 7

Limit of Detection

The limit of detection for HPV 16 E6/7 RNA from HPV positive cells (SiHa cells) was tested (see FIG. 8). Cells were spiked into 1 mL of a pool of negative cervical specimens to model a clinical sample. After spinning down and being lysed with water and heated, buffer was added to the cells (to a concentration of 32.5% buffer, or about 1M guanidine thiocyanate and about 0.7% detergent) and they were placed in a plate to begin the RNA detection assay of the present disclosure. The results show that using the methods of the present disclosure, as few as $1 \times 10^3$ cells are required for HPV E6/7 RNA detection.

Example 8

Lysing Cells Captured by COOH Beads

Figure 9:
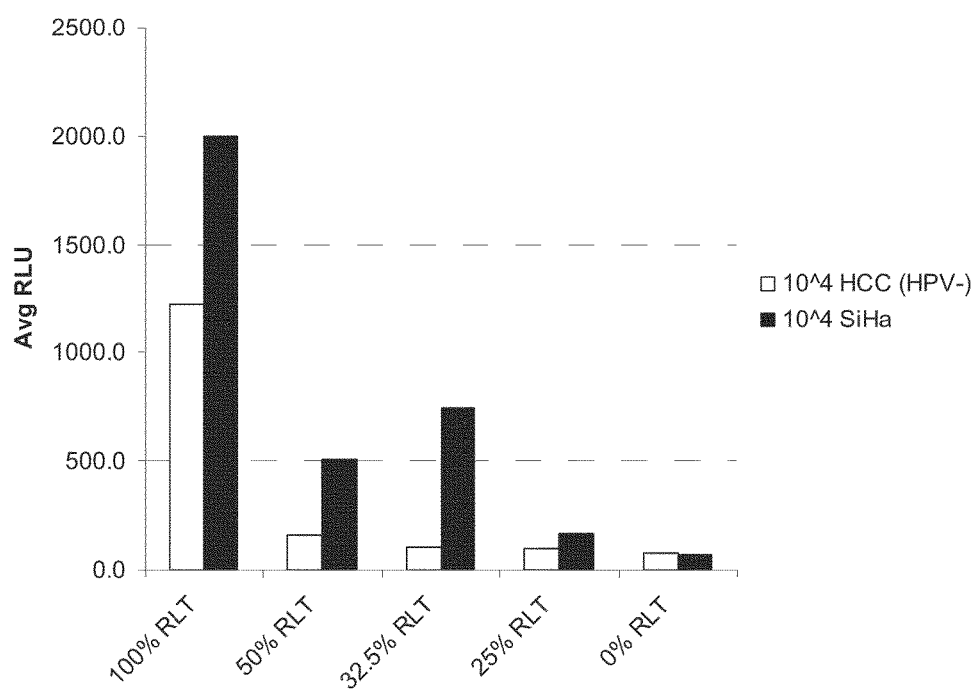
FIG. 9 shows results from tests of various lysis buffers for the ability to lyse cells captured by COOH beads. The data of FIG. 9, along with that of TABLE 1, below, shows the preferred lysis buffer is about 1M guanidine thiocyanate and about 0.7% detergent.

Various lysis buffers were compared for the ability to lyse cells captured by COOH beads (see FIG. 9). The results show that water alone is not enough to lyse cells captured by COOH beads. Either HPV negative or HPV positive cells were spiked into 1 mL of a negative cervical pool. After cells were captured by beads and the supernatant removed, varying concentrations of buffer (containing guanidine thiocyanate and detergent) were added to the samples which were then heated for 15 min at 65° C. Buffer concentration was adjusted to a total of 32.5% for RNA detection using methods of the present disclosure. As seen with the spin-down method, background does decrease with decreasing amounts of salt and detergent. However, at least 32.5% buffer (totaling approximately 1 M salt and 0.7% detergent) is required to lyse the cells enough to release RNA.

Example 9

Time Course of Cell Capture by COOH Beads Shows that Capture of Cells onto the Beads is a Biphasic Reaction A time course of cell capture by COOH beads was conducted (see FIG. 10). Cells were spiked into 1 mL of a negative cervical pool. The baseline number of cells was counted, and at each time point after addition of COOH beads, beads were pelleted for 1.5 min and then the supernatant removed and diluted for counting. Approximately 50% of cells are captured within a minute. Capture then plateaus but at 30 min at least 95% of the cells have been captured. More beads provide slightly more efficient capture.

Example 10

Carboxyl (COOH) Bead Capture is More Efficient than Hypotonic Lysis

HPV 18 positive (HeLa) cells in 1 mL of a pool of negative cervical specimens were prepared with either COOH bead capture or with pelleting and hypotonic lysis. The limit of detection for the carboxyl bead capture method is also approximately 1000 HPV positive cells and the results of the reverse hybrid capture assay show that this method is more efficient for obtaining mRNA from cells (see FIG. 11). While the background is slightly higher when COOH bead capture is used (271 RLUs versus 163 RLUs for hypotonic lysis), both signal:noise and signal—noise (a measure of the total RNA detected) were much higher than when hypotonic lysis is used.

Example 11

Pretreatment Procedure (Hypotonic Lysis) Combined with Detection of Target RNA

The following protocol combines a sample pretreatment procedure (using hypotonic cell lysis) with an RNA detection method of the present disclosure. Spin down cells in tubes for 3 minutes at 1500 relative centrifugal force (RCF). Supernatant was removed and 33.75 µL water was added and pipetted gently to resuspend the pellet. Then, heat for 15 minutes at 65° C. with gentle shaking. Next, add 16.25 µL buffer (about 3 M guanidine thiocyanate and about 2% detergent) and transfer 50 µL sample to wells on the plate. Then, add 10 µL preconjugated streptavidin beads with biotinylated capture probes and incubate the plate for 30 minutes at 60° C. with shaking at 1150 revolutions per minute (RPM). Place the plate on a magnetic rack and let the beads pellet for 1.5 min and then decant and blot plate. Wash twice with Sharp Wash buffer (1 M Tris-HCl, 0.6 M NaCl, 0.25% Tween-20); the first wash should be 2 minutes and the second wash should be 5 minutes. After washing, decant and dry plate well by blotting. To each well, add 65 μL signal amplification probes diluted to 4.2 nM in RNA hybridization buffer. The incubate the plate for 30 minutes at 60° C. with shaking at 1150 RPM. Place the plate on magnetic rack for 3 min, decant, and dry wells. Add 35 μL. Digene Hybrid Capture 2 kit Detection Reagent 1 (alkaline phosphatase-conjugated antibodies to RNA:DNA hybrids in buffered solution with 0.05% (w/v) of sodium azide, and with no RNase) into each well and incubate the plate for 30 minutes at 45° C. Place the plate on the magnetic rack, decant, and blot. Wash the plate five times with buffer comprising 40 mM Tris-HCl, 100 mM NaCl, 0.5% Triton X-100, allow plate to sit 1 minute per wash. Then, decant and dry the wells. Next, add 45 μL Digene Hybrid Capture 2 kit Detection Reagent 2 (CDP-Star® reagent with Emerald II™, a chemiluminescent substrate) to each well. Protect from light and incubate the plate for 15 minutes at room temperature with shaking at 300 RPM. Read the plate on a luminometer.

Example 12

Pretreatment Procedure (COOH Bead Capture) Combined with Detection of Target RNA The following protocol combines carboxyl bead capture sample preparation with an RNA detection method of the present disclosure. To each sample, add 8 μL carboxyl (COOH) beads (2 mL well plate) and shake at 800 RPM for 30 minutes at room temperature. Place the plate on a magnetic rack for 2 minutes to pellet beads. Remove supernatant with vacuum and resuspend in 50 μL 32.5% buffer (about 1M guanidine thiocyanate and about 0.7% detergent). Then, shake at 1000 RPM for 15 minutes at 65° C. Place the plate on a magnetic rack, pellet the beads, and transfer supernatant to new wells. Then, add 10 μL preconjugated streptavidin beads with biotinylated capture probes and incubate the plate for 30 minutes at 60° C. with shaking at 1150 RPM. Place the plate on a magnetic rack and let the heads pellet for 1.5 min and then decant and blot plate. Wash twice with Sharp Wash buffer (1 M Tris-HCl, 0.6 M NaCl, 0.25% Tween-20); the first wash should be 2 minutes and the second wash should be 5 minutes. After washing, decant and dry plate well by blotting. To each well, add 65 μL signal amplification probes diluted to 4.2 nM in RNA hybridization buffer. The incubate the plate for 30 minutes at 60° C. with shaking at 1150 RPM. Place the plate on magnetic rack for 3 min, decant, and dry wells. Add 35 μL Detection Reagent 1 (alkaline phosphatase-conjugated antibodies to RNA:DNA hybrids in buffered solution with 0.05% (w/v) of sodium azide, and with no RNase) into each well and incubate the plate for 30 minutes at 45° C. Place the plate on the magnetic rack, decant, and blot. Wash the plate five times with buffer comprising 40 mM Tris-HCl, 100 mM NaCl, 0.5% Triton X-100, allow plate to sit 1 minute per wash. Then, decant and dry the wells. Next, add 45 μL Detection Reagent 2 (CDP-Star® reagent with Emerald II™, a chemiluminescent substrate) to each well. Protect from light and incubate the plate for 15 minutes at room temperature with shaking at 300 RPM. Read the plate on a luminometer.

Example 13

Streptavidin Bead-Biotinylated Probe Conjugation

The following protocol provides a method of forming DNA capture probes bound to magnetic beads. Vortex and sonicate Seradyn dsMag streptavidin beads (Seradyn part #3015210301050, Thermo Fisher Scientific, Inc.). Add 5 μL beads to 250 μL bead conjugation buffer (1×PBS; 0.15 M NaCl). Pull down beads on magnetic rack and was twice with bead conjugation wash buffer (above 0.5% Tween-20). Resuspend beads with 45 nM of each DNA capture probe in bead conjugation buffer. Incubate for 30 minutes at 37° C. with shaking at 1150 RPM. Pull down beads and wash three times with bead conjugation wash buffer. Resuspend in 250 μL Blocker buffer (casein-based) from Digene Hybrid Capture 2 to yield 50× beads.

Example 14

Reverse Hybrid Capture Assay

Reverse hybrid capture detects mRNA by first capturing the target RNA onto complementary biotinylated DNA probes that are conjugated to magnetic streptavidin beads. This probe-bead complex may be preconjugated and is stable at 4° C. for several months. This capture step requires 30 min and should occur at 60° C. with constant shaking. The beads with the captured target are then washed so that any non-target RNA sequences are removed. Because the hybrid capture antibody binds to individual DNA-RNA hybrids, it is preferable to cover the target RNA with DNA probes (e.g., DNA capture probe and amplification probes) to achieve the maximal signal (see, e.g., FIGS. 1 & 2). Thus, additional probes are then hybridized to the target mRNA. Because only the target is present at this point (because non-target RNA has been washed away), these probes need not be sequence-specific but rather may cover the full length of the gene, excluding regions that are already covered by the biotinylated DNA probes. These "signal amplification" probes are diluted to a working concentration of 4.2 nM. This hybridization also occurs at 60° C. for 30 min at a pH of around 7.8, preferably with shaking. The hybridization is then followed by detection with the hybrid capture antibody system: exposure to Detection Reagent 1 (alkaline phosphatase-conjugated antibodies to RNA:DNA hybrids in buffered solution with 0.05% (w/v) of sodium azide, and with no RNase) for 30 min at 45° followed by extensive washing and subsequent addition of Detection Reagent 2 (CDP-Star® reagent with Emerald II™, a chemiluminescent substrate) for 15 min at room temperature. The signal is read on a luminometer. This post-analytic portion of the assay takes approximately 2 h 15 min.

Example 15

Effect of Adding Unlabeled Signal Amplification Probe

The signal is relatively low for a RNA target captured with only 3 or 5 biotinylated DNA capture probes and no unlabeled signal probes. The signal is substantially higher when unlabeled probes are hybridized to the target before detection with hybrid-capture antibody and luminescence technology. The reverse hybrid-capture assay is used to detect RNA. In this experiment, a variable number of biotinylated DNA capture probes were conjugated to streptavidin beads (see FIG. 4). The target was the E6/7 gene of HPV 16. The assay was performed with each set of beads with and without the addition of signal amplification probes (one-versus two-step assay, respectively). When no unlabeled DNA probes for signal amplification were added (one-step assay; gray bars), the signal increased with the amount of coverage provided by the biotinylated capture probes. However, when unlabeled DNA probes for signal amplification were added (two-step assay; black bars), the signal was much higher than in the one-step assay when only 1, 3, or 5 capture probes were used. In the two-step assay, optimal signal was achieved with as few as 3 to 5 capture probes.

Example 16

Length of mRNA Transcript Determined by Molecular Ruler Method

Figure 12:
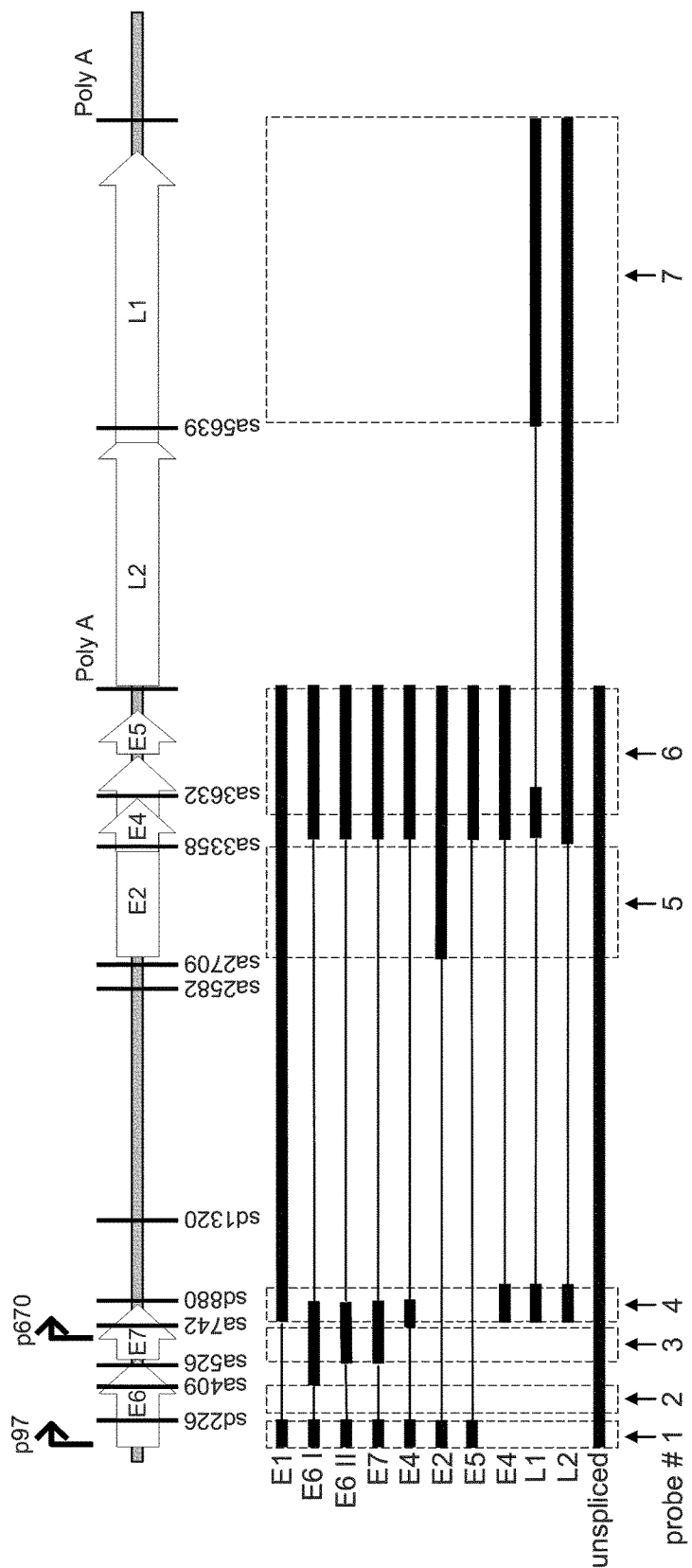
FIG. 12 is a diagram depicting capture and signal probe design regions. The length of HPV transcripts can be "characterized" by capture onto magnetic beads with specific capture oligos that capture specific targets and detected with various sets of unlabeled oligonucleotides used to extend the length of the hybrid region. Signal will result if the capture RNA bears the sequence that is complementary to the detection probes that are used. Signal output will increase with successive addition of amplification signal probes until maximum length is reached where the signal will plateau. The various HPV transcripts for HPV 16 are shown. The regions denoted by the dashed boxes are designated for probe design.
Figure 13:
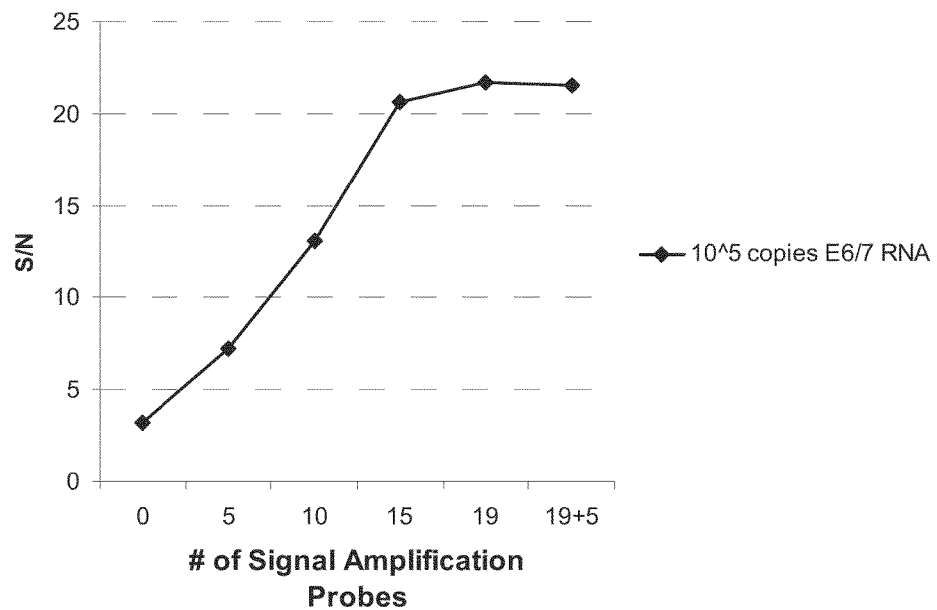
FIG. 13 shows increasing signal as the number of signal amplification probes is increased. In this way, an RNA transcript length may be measured by the increasing signal generated by the increased number of consecutive detection probes.

The length of HPV transcripts can be "measured" by capture onto magnetic beads and detection with unlabeled oligonucleotides used in order to extend the length of the hybrid region. Signal output will increase with successive addition of amplification signal probes until maximum length is reached, where the signal will plateau. The various HPV transcripts for HPV 16 are shown schematically in FIG. 12. The numbered regions 1 through 7 (FIG. 12) are designated for probe design. For instance, the E6/7 gene transcript can be captured from a sample using the DNA capture probe 3 and the combination of signal amplification probes will determine the signal output. If the variant form present is full length and the combination of amplification probes covers the entire length of the transcript, the signal will be strong. If E6/7 the variant form present is spliced and a subset of signal probes is used (e.g., probes 1 and 6), then the signal output will be somewhat weaker compared to signal from full-length/unspliced E6/7 (see TABLE 3). If the E6/7 variant form is spliced and integrated, it will provide a much weaker signal (see TABLE 3). The stronger signal is indicative of a greater number of targets and a certain disease state. E6/7 spliced integrated variant provides a weaker signal and is indicative of fewer targets captured, and thus less expression of this gene. It is also indicative of a different disease state. TABLE 3 shows the expected signal resulting from the combined use of the listed probes (shown in FIG. 12) from various regions of HPV 16.

TABLE 3

| mRNA Target | Splice Form | Capture Probes | Signal Probes | Signal Output |
|---|---|---|---|---|
| E6/7 | unspliced/full length | 2 | 1, 2, 3, 4, 5, 6, 7 | ++++++ |
|  | spliced | 3 | 1, 6 | ++++ |
|  | spliced/integrated | 3 | 1, 6 | + |
| E2 | episomal | 5 | 1, 5, 6 | ++++++ |
|  | integrated | 5 | 1, 5, 6 | + |
| L1 | spliced | 7 | 4, 6, 7 | ++++++ |

Referring again to FIG. 12 and TABLE 3, the signal contributed by non-spliced transcripts hybridizing to capture probe #2 (for example) may be subtracted from the signal generated using other capture probes to determine the degree of signal arising from spliced transcripts alone. The combination of signal amplification probes will determine the extent of coverage on the target mRNA and hence, signal output. Comparison of the signal output resulting from different combinations of amplification probes will indicate the presence of particular mRNA splice form variants. In this way, this method is a "molecular ruler" in that the signal output is dependent upon the splice form present and can indicate progression of disease state.

Example 17

Detection of Elevated Early:Late mRNA Ratio

Figure 14:
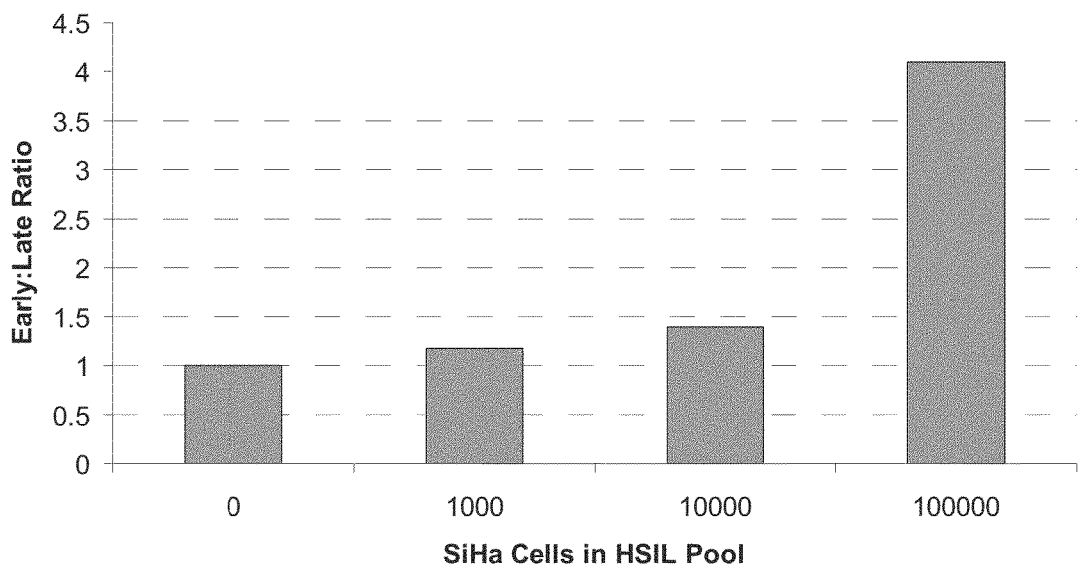
FIG. 14 shows that a fraction of cells with a high early:late HPV mRNA ratio may be detected against a background of cells with a low ratio. For this FIG. 14, SiHa cells (cervical cancer cell line) were added to a pool of cervical specimens (each diagnosed with a high-grade HPV-related lesion). The SiHa cells incorporate a high ratio of HPV early transcripts: HPV late transcripts, which is a common characteristic of cervical cancer. The sample mimicked a specimen that has cancer cells among pre-cancerous lesion cells. The results show that the invented assay will detect cancer cells in a pool of more benign lesion cells.

The methods of the present disclosure enable detection of a ratio of early and late HPV mRNA transcripts, which may be indicative of progressing HPV-related cervical disease. The described assay detected a high early:late mRNA ratio of SiHa cells (cancer cell line) against a background of HPV-positive specimens (FIG. 14). Capture and detection DNA probes were designed to detect early transcripts and late transcripts of HPV. These two assays were performed concurrently on the same samples, and the ratio of the resulting signals indicates the ratio of the early and late HPV transcripts. To mimic specimens comprising a few cancer cells mixed with cells of pre-cancerous lesion, pools of HSIL specimens (high-grade squamous intraepithelial lesion, per Bethesda System for cervical cytology) were spiked with known numbers of SiHa cells (as indicated along the x-axis), and then assayed via the methods of the present disclosure (see, e.g., EXAMPLE 12). As indicated by FIG. 14, a fraction of cells with a high E6/7 mRNA ratio may be detected against a background of cells with a low ratio.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A non-target amplification reverse hybrid capture method of detecting the presence of a target human papillomavirus (HPV) RNA, the method comprising:
    (a) providing the target human HPV RNA by a method comprising:
        (i) incubating a biological sample comprising a cell containing the target HPV RNA with carboxyl beads under conditions sufficient for the cell to bind to the carboxyl beads;
        (ii) isolating the beads;
        (iii) lysing the cell attached to the isolated beads; and
        (iv) isolating the beads from the lysed biological sample, wherein the resulting supernatant contains the target HPV RNA for detection;
    (b) providing at least one DNA capture probe, wherein the at least one DNA capture probe is bound to a support;
    (c) hybridizing the target RNA to said at least one DNA capture probe, yielding a target RNA:DNA capture probe complex;
    (d) isolating the target RNA:DNA capture probe complex by removal of non-target RNA sequences;
    (e) providing a first combination of DNA amplification probes, and hybridizing said first combination of DNA amplification probes to said target RNA:DNA capture probe complex, yielding a target RNA:DNA capture/amplification probe complex, wherein said DNA amplification probes are from about 15 to about 200 bases in length and are designed to be complementary over the length of the target HPV RNA and combined in mixtures to cover specific genes, excluding regions that are already covered by the at least one DNA capture probe, in order to allow detection of specific splice forms of the RNA;

(f) providing an anti-RNA:DNA hybrid antibody, and incubating said target RNA:DNA capture/amplification probe complex with said antibody, yielding a target RNA:DNA:antibody complex;

(g) detecting said antibody, and comparing the detection results with results produced from a different combination of DNA amplification probes, wherein the comparing indicates the presence of a particular RNA splice-form, wherein the at least one DNA capture probe and the DNA amplification probes are complementary to RNA from HPV, and wherein said carboxyl beads do not comprise an immobilized ligand.

2. The method of claim 1, wherein said antibody is conjugated to a detectable marker, and wherein said detecting comprises detecting the marker.

3. The method of claim 2, wherein the detectable marker is selected from the group consisting of alkaline phosphatase and horseradish peroxidase.

4. The method of claim 1, wherein said detecting comprises providing a second antibody that binds to said anti-RNA:DNA hybrid antibody, wherein said second antibody is conjugated to a detectable marker, and wherein said detecting further comprises detecting the marker.

5. The method of claim 1 wherein the support comprises a magnetic bead.

6. The method of claim 5, wherein said at least one DNA capture probe is conjugated to a biotin molecule, and wherein said support is conjugated to at least one streptavidin molecule.

7. The method of claim 1, wherein the at least one DNA capture probe is from about 15 to about 200 bases in length.

8. The method of claim 1, wherein the at least one DNA capture probe and the at least one DNA amplification probe are complementary to RNA from HPV high risk types 16, 18, 31, 33, 35, 39, 45, 51, 52, 56, 58, 59, 68, 26, 66, 73, and 82.

9. The method of claim 1, wherein the first combination of DNA amplification probes and the different combination of DNA amplification probes comprise degenerate signal amplification probes that cover predicted splice form sequences.

\* \* \* \* \*